United States Patent
Wiltafsky et al.

(10) Patent No.: US 11,644,452 B2
(45) Date of Patent: May 9, 2023

(54) METHOD FOR THE DETERMINATION OF PROCESSING INFLUENCES ON THE NUTRITIONAL VALUE OF FEEDSTUFF RAW MATERIALS

(71) Applicant: Evonik Operations GmbH, Essen (DE)

(72) Inventors: Markus Wiltafsky, Moembris (DE); Ingolf Reimann, Reinheim (DE); Johann Fickler, Moemlingen (DE); Meike Rademacher-Heilshorn, Wulsbuettel (DE)

(73) Assignee: Evonik Operations GmbH, Essen (DE)

( * ) Notice: Subject to any disclaimer, the term of this patent is extended or adjusted under 35 U.S.C. 154(b) by 909 days.

(21) Appl. No.: 16/485,054

(22) PCT Filed: Feb. 12, 2018

(86) PCT No.: PCT/EP2018/053396
§ 371 (c)(1),
(2) Date: Aug. 9, 2019

(87) PCT Pub. No.: WO2018/146295
PCT Pub. Date: Aug. 16, 2018

(65) Prior Publication Data
US 2019/0360986 A1    Nov. 28, 2019

Related U.S. Application Data

(63) Continuation of application No. 15/431,597, filed on Feb. 13, 2017, now abandoned.

(30) Foreign Application Priority Data

Feb. 13, 2017  (EP) .................................... 17155896

(51) Int. Cl.
*G01N 33/02*      (2006.01)
*A23K 20/142*     (2016.01)
(Continued)

(52) U.S. Cl.
CPC .............. *G01N 33/02* (2013.01); *A23K 10/30* (2016.05); *A23K 20/142* (2016.05); *A23K 50/00* (2016.05);
(Continued)

(58) Field of Classification Search
CPC ........... G01J 3/02; G01N 33/02; G01N 21/35; G01N 21/3563; G01N 21/359;
(Continued)

(56) References Cited

U.S. PATENT DOCUMENTS 5,709,894 A    1/1998  Julien
5,783,238 A    7/1998  Julien
(Continued)

FOREIGN PATENT DOCUMENTS

EP     1 145 645 A1    10/2001
NZ       312221 A       5/2002
(Continued)

OTHER PUBLICATIONS

International Search Report and Written Opinion dated Mar. 14, 2018 in PCT/EP2018/053396 file Feb. 12, 2018.
(Continued)

*Primary Examiner* — Abdullahi Nur
(74) *Attorney, Agent, or Firm* — Oblon, McClelland, Maier & Neustadt, L.L.P.

(57) ABSTRACT

The present invention relates to a method for the determination of processing influences on the quality of feedstuff raw materials and/or feedstuffs, in which the processing conditions indicator of the of feedstuff raw materials and/or feedstuffs is determined and the specific digestibility coef-
(Continued)

Standardized ileal digestibility coefficent of methionine (SID$_{Met}$) in full-fat soybeans for poultry (SID$_{Met}$ = − 0.3581×PCI$^2$ + 8.679×PCI + 33.624)

ficient of an amino acid of a feedstuff raw material and/or feedstuff in an animal species is determined. The present invention also relates to a process for the optimization of feedstuffs considering the determined processing influences and the thus obtained and/or obtainable feedstuffs.

14 Claims, 15 Drawing Sheets

(51) Int. Cl.
*A23K 50/00* (2016.01)
*A23K 10/30* (2016.01)
*G01N 21/3563* (2014.01)
*G01N 21/359* (2014.01)

(52) U.S. Cl.
CPC ....... *G01N 21/359* (2013.01); *G01N 21/3563* (2013.01)

(58) Field of Classification Search
CPC ........ A23K 10/30; A23K 1/14; A23K 20/142; A23K 50/00; A23K 50/10; A23K 50/30; A23K 50/75; G06K 17/00
See application file for complete search history.

(56) References Cited

U.S. PATENT DOCUMENTS

| | | | |
|---|---|---|---|
| 5,863,574 A | 1/1999 | Julien | |
| 6,114,699 A * | 9/2000 | Barton | G01N 21/3563 250/341.8 |
| 6,312,710 B1 | 11/2001 | Julien | |
| 6,532,420 B1 | 3/2003 | Haeffner et al. | |
| 6,907,351 B2 * | 6/2005 | Julia | G01N 21/359 702/30 |
| 2002/0090442 A1 * | 7/2002 | Haeffner | G01N 33/02 426/623 |
| 2010/0247707 A1 | 9/2010 | Kobler | |
| 2012/0317675 A1 | 12/2012 | Schillinger | |
| 2014/0205711 A1 | 7/2014 | Kobler | |

FOREIGN PATENT DOCUMENTS

| | | |
|---|---|---|
| SU | 1354107 A1 | 11/1987 |
| WO | WO 97/02489 | 1/1997 |
| WO | WO 01/15548 A1 | 3/2001 |
| WO | WO 2011/109624 A1 | 9/2011 |

OTHER PUBLICATIONS

Mills, R., "Evonik's Amino NIR-NIR for the feed industry," http://nirperformance.com/2012/10/24/evoniks-amino-nir/, Oct. 24, 2012, pp. 1-4, XP055301934.

Rokey, G. J., et al., "Feed extrusion process description," Revista Brasileira de Zootecnia, vol. 39, 2010, www.scielo.br/pdf/rbz/v39sspe/55.pdf, pp. 510-518, XP055380349.

Hickling, D., "Canadian Feed Peas Industry Guide," Pulse Canada, Third Edition, 2003, pp. 1-36, XP055322748.

* cited by examiner

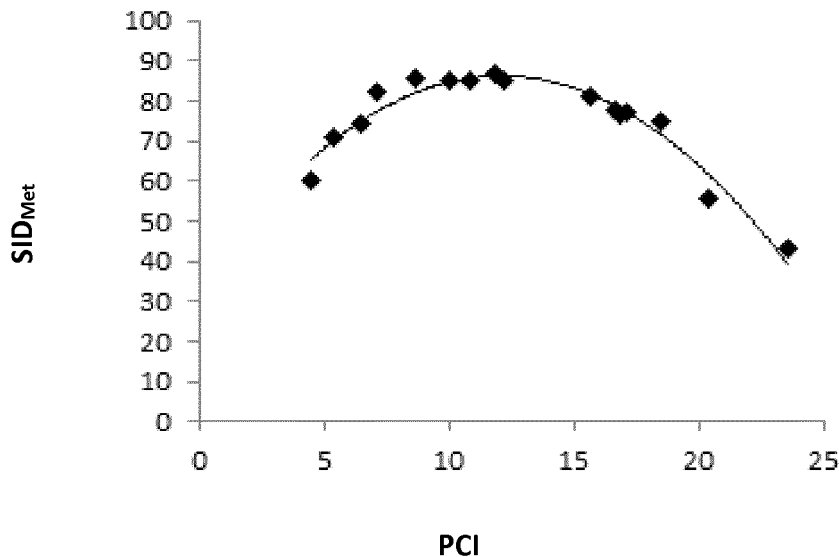
Fig. 1: Standardized ileal digestibility coefficent of methionine ($SID_{Met}$) in full-fat soybeans for poultry ($SID_{Met} = -0.3581 \times PCI^2 + 8.679 \times PCI + 33.624$)
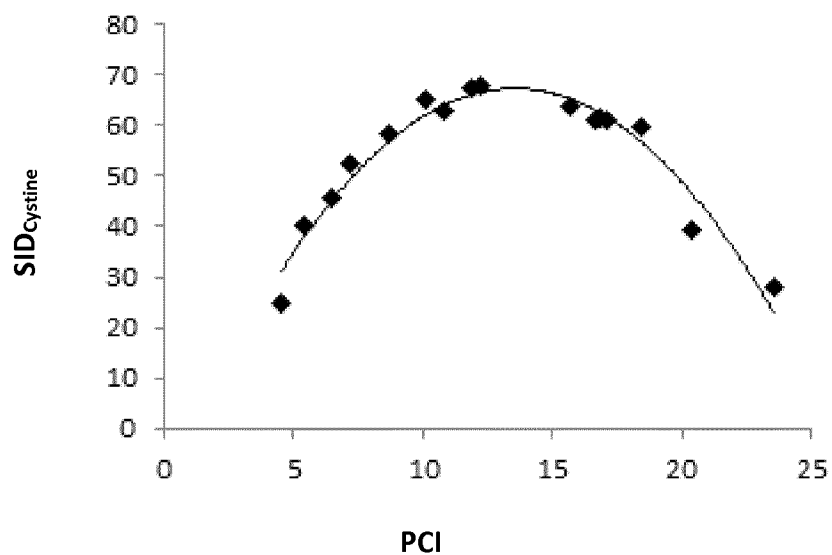
Fig. 2: Standardized ileal digestibility coefficent of cystine ($SID_{Cystine}$) in full-fat soybeans for poultry ($SID_{Cystine} = -0.442 \times PCI^2 + 11.983 \times PCI + 13.905$)

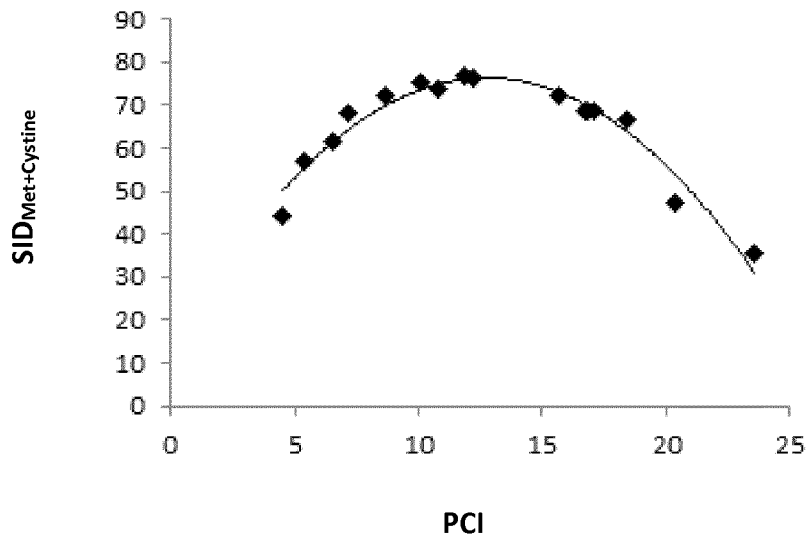
Fig. 3: Standardized ileal digestibility coefficent of methionine and cysteine ($SID_{Met+Cystine}$) in full-fat soybeans for poultry ($SID_{Met+Cystine} = -0.3861 \times PCI^2 + 9.8435 \times PCI + 13.53$)
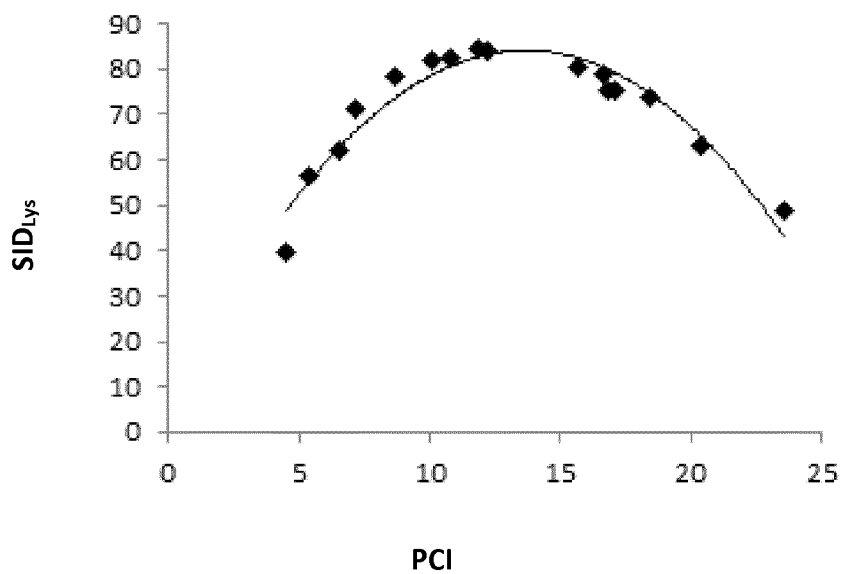
Fig. 4: Standardized ileal digestibility coefficent of lysine ($SID_{Lys}$) in full-fat soybeans for poultry ($SID_{Lys} = -0.4187 \times PCI^2 + 11.462 \times PCI + 5.6474$)

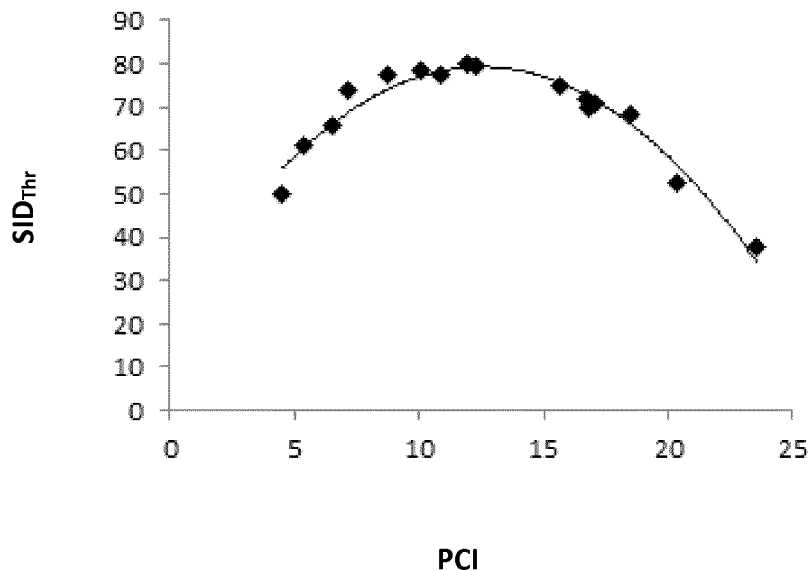
Fig. 5: Standardized ileal digestibility coefficent of threonine (SID$_{Thr}$) in full-fat soybeans for poultry (SID$_{Thr}$ = - 0.368×PCI$^2$ + 9.2054×PCI + 12.772)
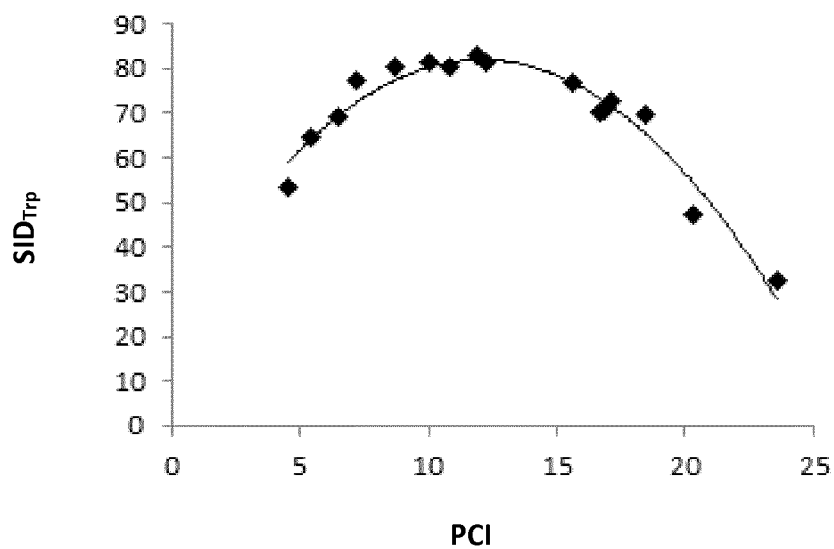
Fig. 6: Standardized ileal digestibility coefficent of tryptophan (SID$_{Trp}$) in full-fat soybeans for poultry (SID$_{Trp}$ = - 0.4046×PCI$^2$ + 9.7674×PCI + 23.052)

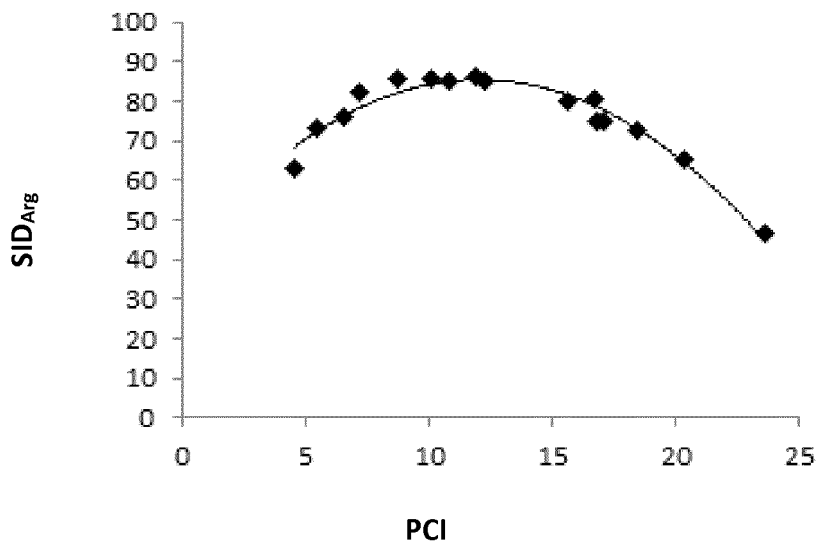
Fig. 7: Standardized ileal digestibility coefficent of arginine ($SID_{Arg}$) in full-fat soybeans for poultry ($SID_{Arg} = -0.3033 \times PCI^2 + 7.3008 \times PCI + 41.512$)
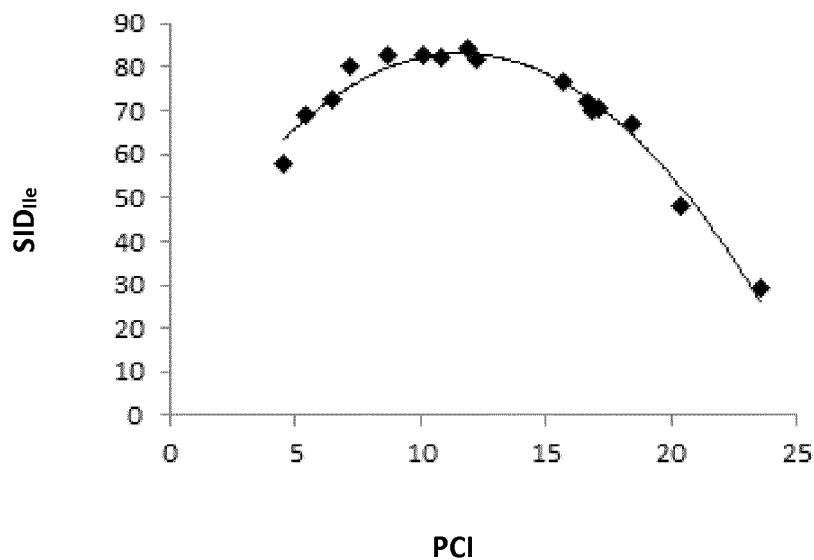
Fig. 8: Standardized ileal digestibility coefficent of isoleucine ($SID_{Ile}$) in full-fat soybeans for poultry ($SID_{Ile} = -0.3974 \times PCI^2 + 9.211 \times PCI + 29.802$)

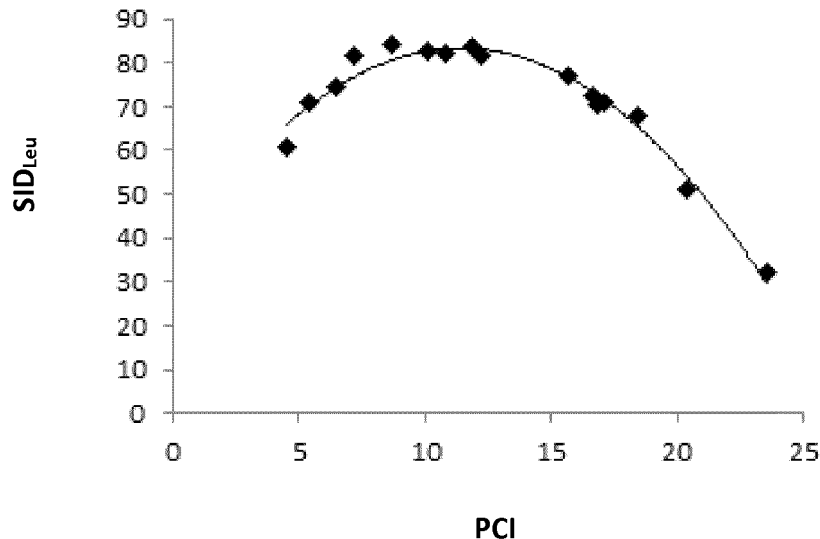
Fig. 9: Standardized ileal digestibility coefficent of leucine ($SID_{Leu}$) in full-fat soybeans for poultry ($SID_{Leu} = -0.3639 \times PCI^2 + 8.3187 \times PCI + 35.843$)
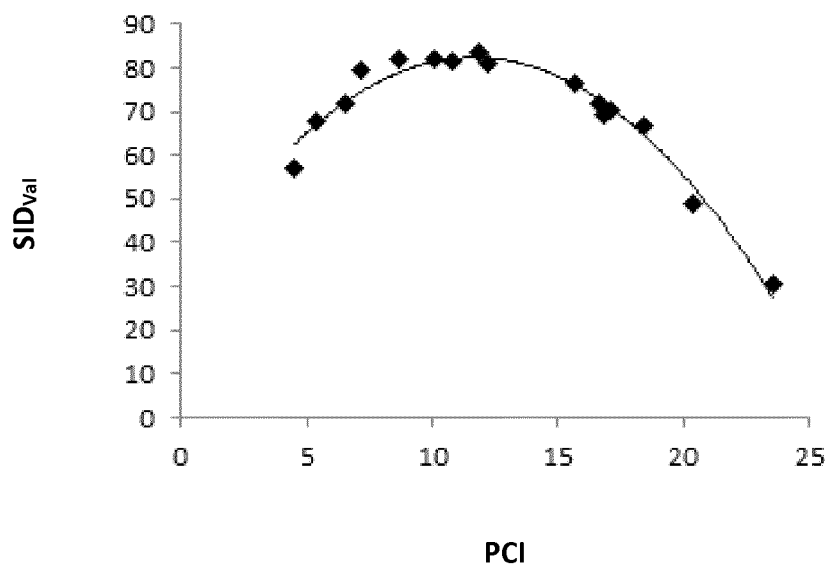
Fig. 10: Standardized ileal digestibility coefficent of valine ($SID_{Val}$) in full-fat soybeans for poultry ($SID_{Val} = -0.388 \times PCI^2 + 9.0608 \times PCI + 29.464$)

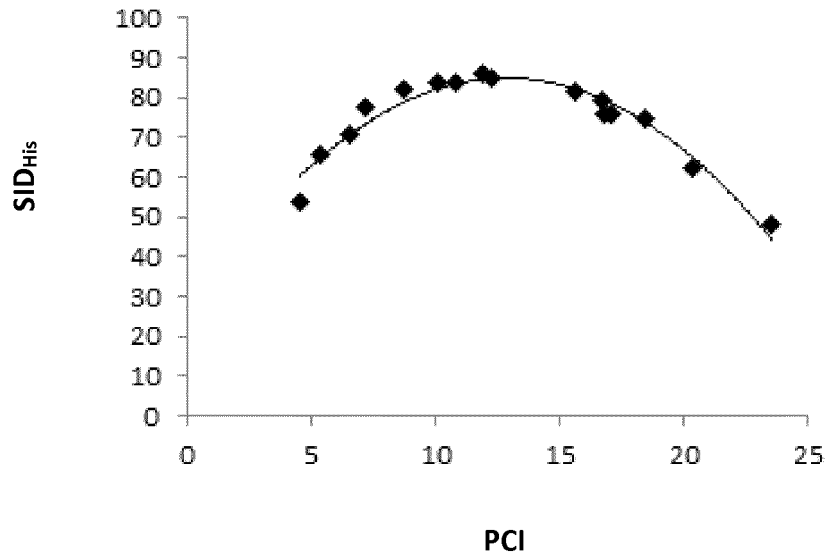
Fig. 11: Standardized ileal digestibility coefficent of histidine ($SID_{His}$) in full-fat soybeans for poultry ($SID_{His}= -0.3554 \times PCI^2 + 9.1547 \times PCI + 25.938$)
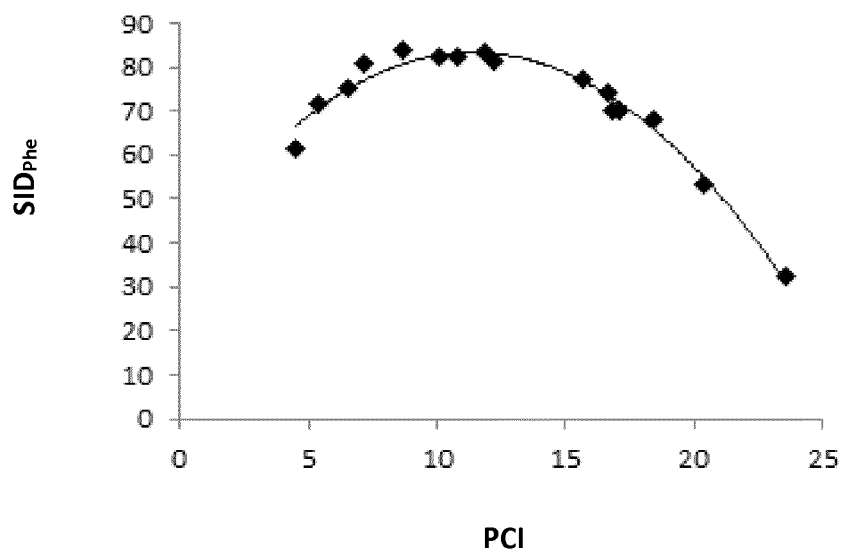
Fig. 12: Standardized ileal digestibility coefficent of phenylalanine ($SID_{Phe}$) in full-fat soybeans for poultry ($SID_{Phe}= -0.3523 \times PCI^2 + 8.0374 \times PCI + 37.432$)

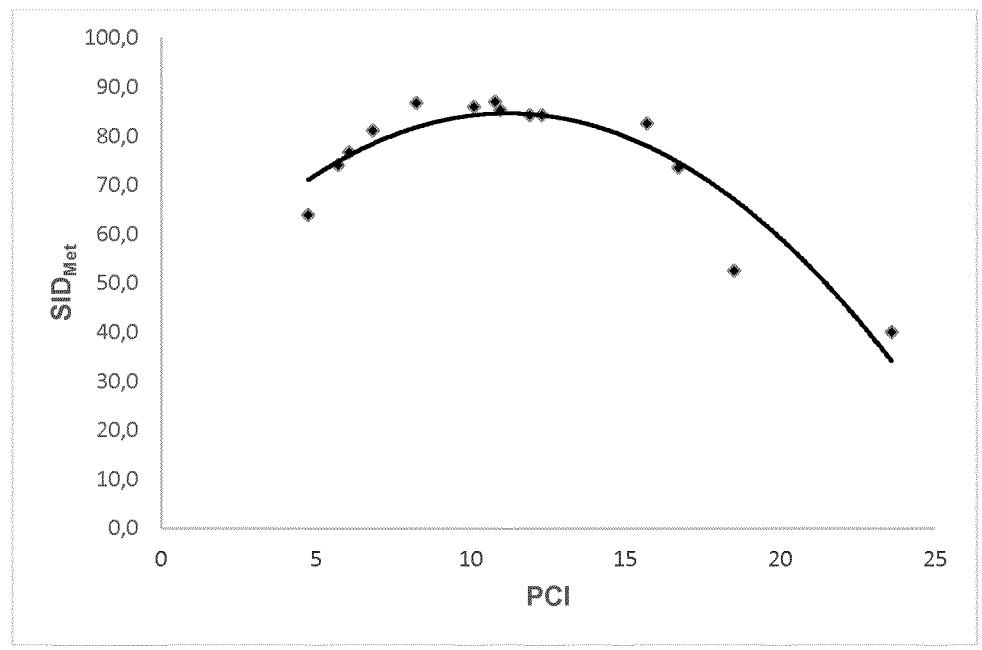
Fig. 13: Standardized ileal digestibility coefficent of methionine (SID$_{Met}$) in full-fat soybeans for pigs
(SID$_{Met}$ = − 0.3286 × PCI$^2$ + 7.3561 × PCI + 43.444)
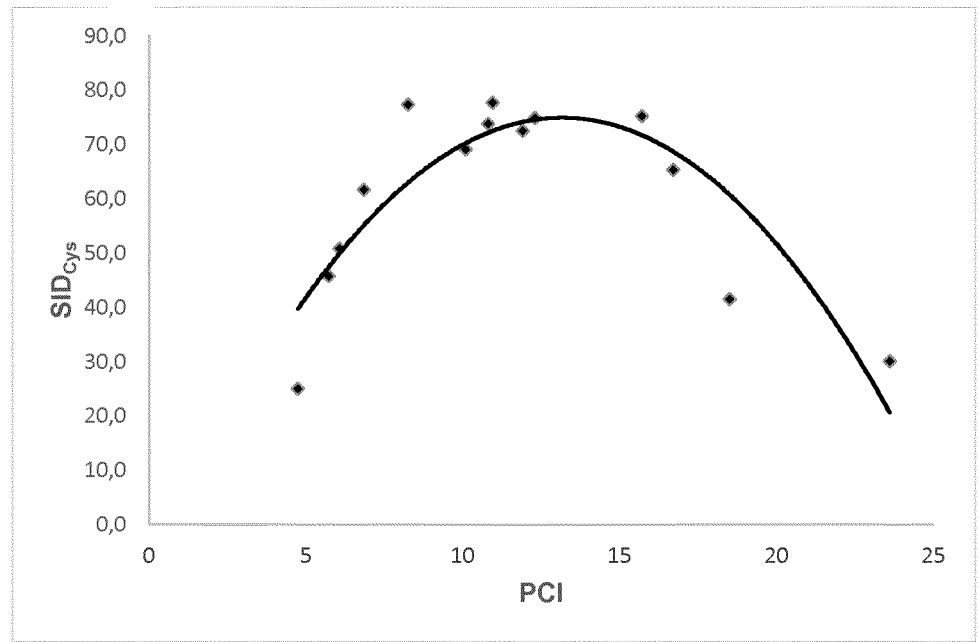
Fig. 14: Standardized ileal digestibility coefficent of cystine (SID$_{Cys}$) in full-fat soybeans for pigs
(SID$_{Cys}$ = − 0.4982 × PCI$^2$ + 13.115 × PCI − 11.392)

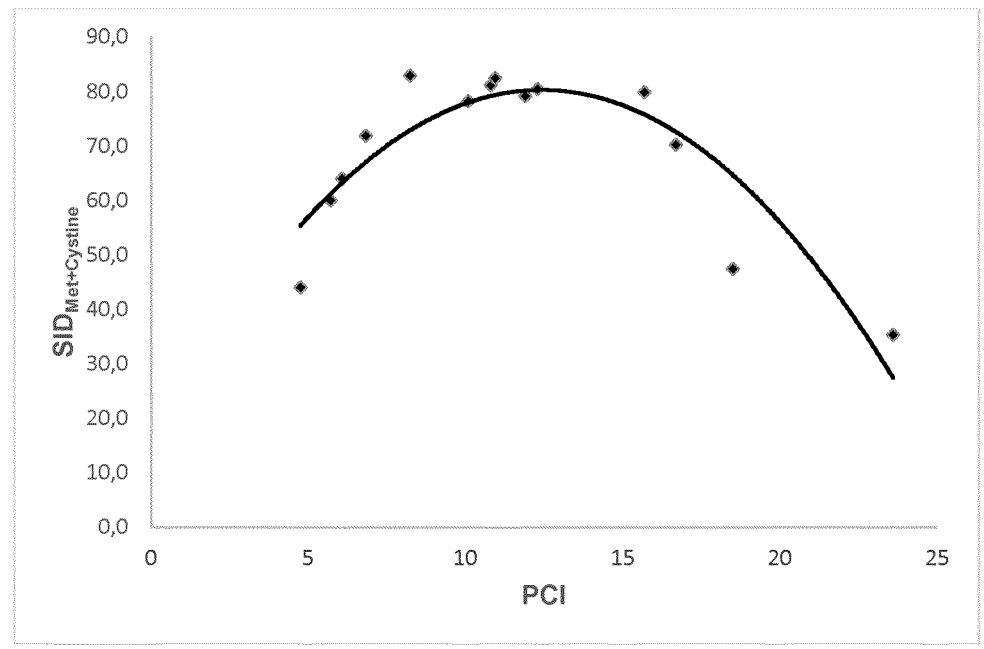
Fig. 15: Standardized ileal digestibility coefficent of methionine and cystine ($SID_{Met+Cystine}$) in full-fat soybeans for pigs ($SID_{Met+Cystine} = -0.4237 \times PCI2 + 10.534 \times PCI + 14.77$)
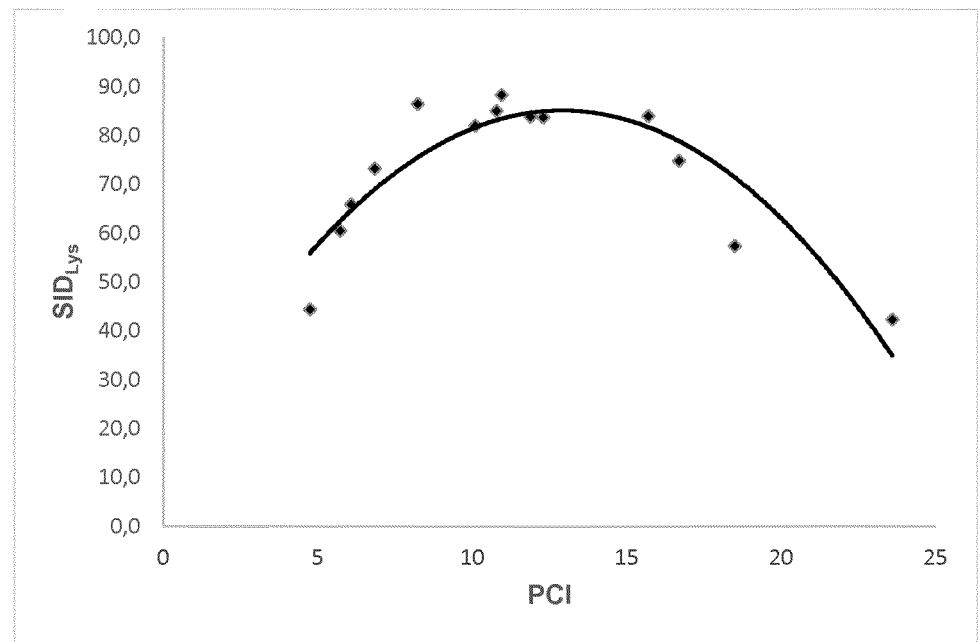
Fig. 16: Standardized ileal digestibility coefficent of lysine ($SID_{Lys}$) in full-fat soybeans for pigs ($SID_{Lys} = -0.4397 \times PCI^2 + 11.359 \times PCI + 11.75$)

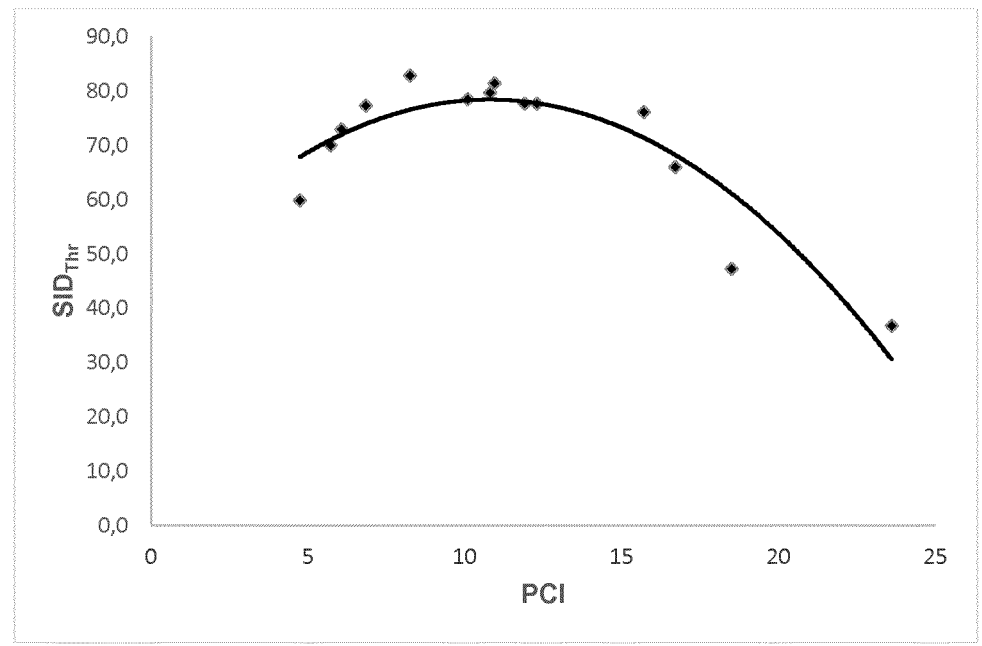
Fig. 17: Standardized ileal digestibility coefficent of threonine (SID$_{Thr}$) in full-fat soybeans for pigs (SID$_{Thr}$ = - 0.291 × PCI$^2$ + 6.2769 × PCI + 44.594)
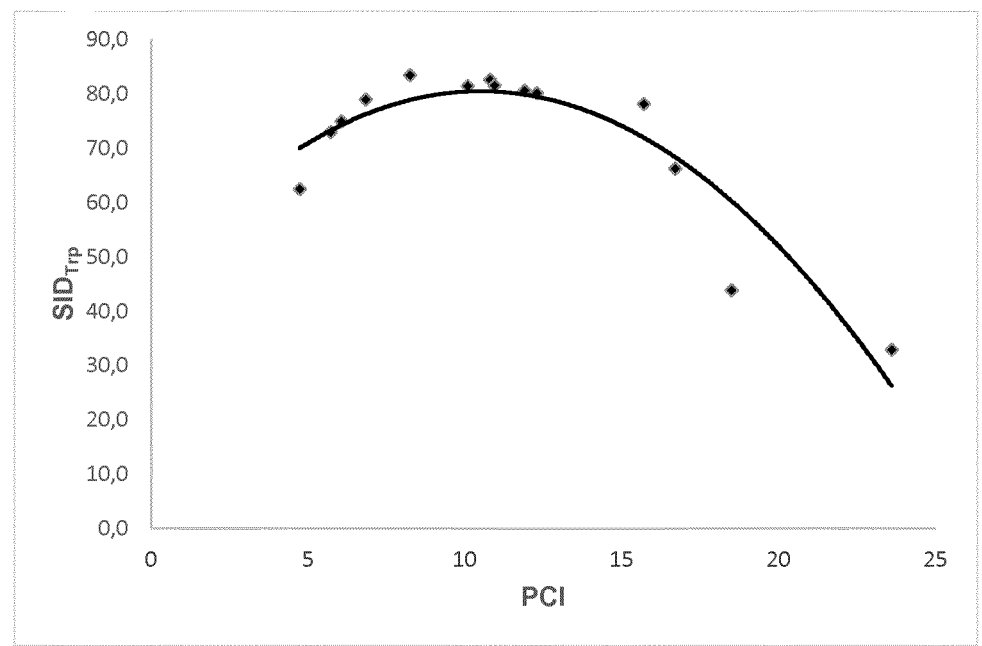
Fig. 18: Standardized ileal digestibility coefficent of thryptophane (SID$_{Trp}$) in full-fat soybeans for pigs (SID$_{Trp}$ = - 0.3167 × PCI$^2$ + 6.6559 × PCI + 45.534)

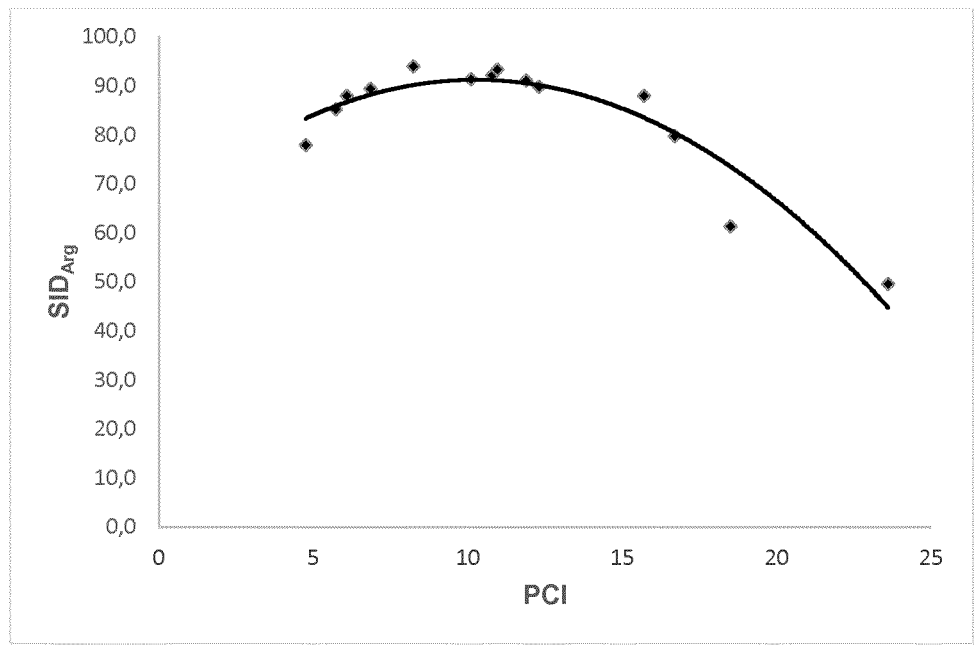
Fig. 19: Standardized ileal digestibility coefficent of arginine ($SID_{Arg}$) in full-fat soybeans for pigs ($SID_{Arg} = -0.261 \times PCI^2 + 5.3573 \times PCI + 63.685$)
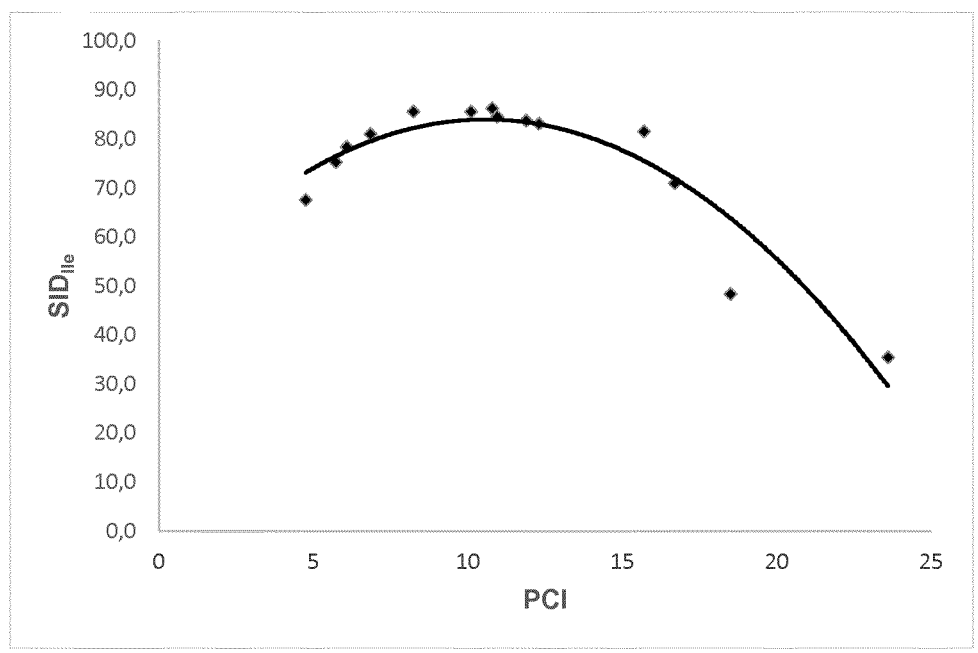
Fig. 20: Standardized ileal digestibility coefficent of isoleucine ($SID_{Ile}$) in full-fat soybeans for pigs ($SID_{Ile} = -0.3204 \times PCI^2 + 6.7739 \times PCI + 48.135$)

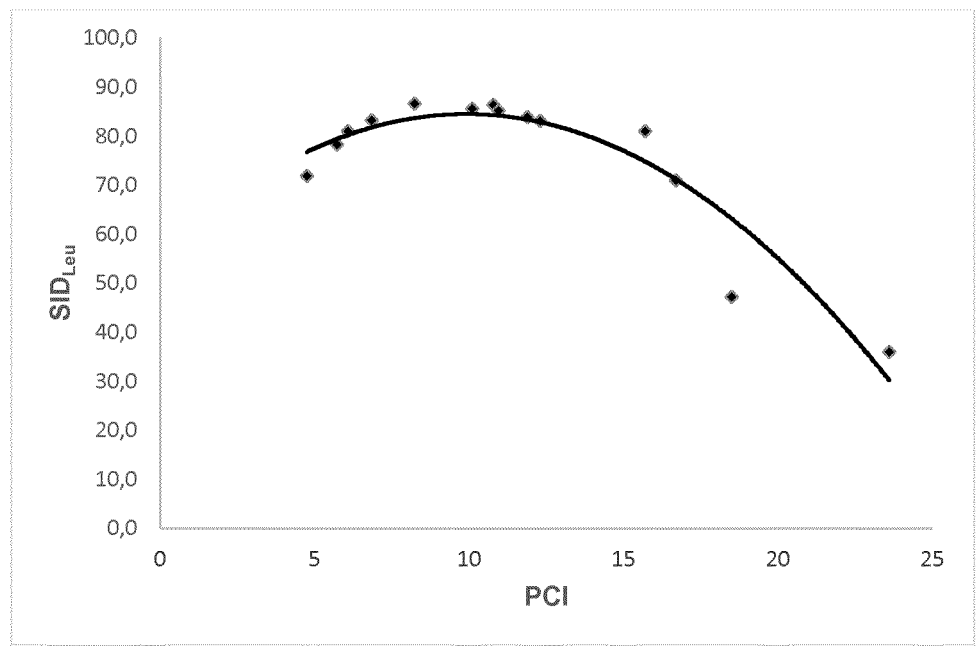
Fig. 21: Standardized ileal digestibility coefficent of leucine (SID$_{Leu}$) in full-fat soybeans for pigs (SID$_{Leu}$ = - 0.2901 × PCI$^2$ + 5.7556 × PCI + 55.925)
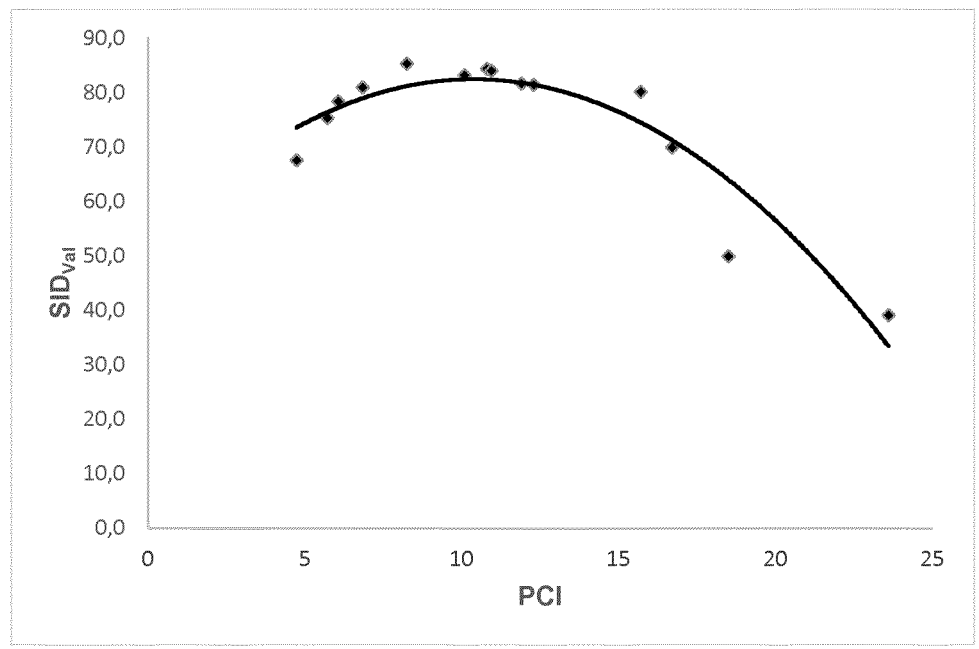
Fig. 22: Standardized ileal digestibility coefficent of valine (SID$_{Val}$) in full-fat soybeans for pigs (SID$_{Val}$ = - 0.2801 × PCI$^2$ + 5.8136 × PCI + 52.234)

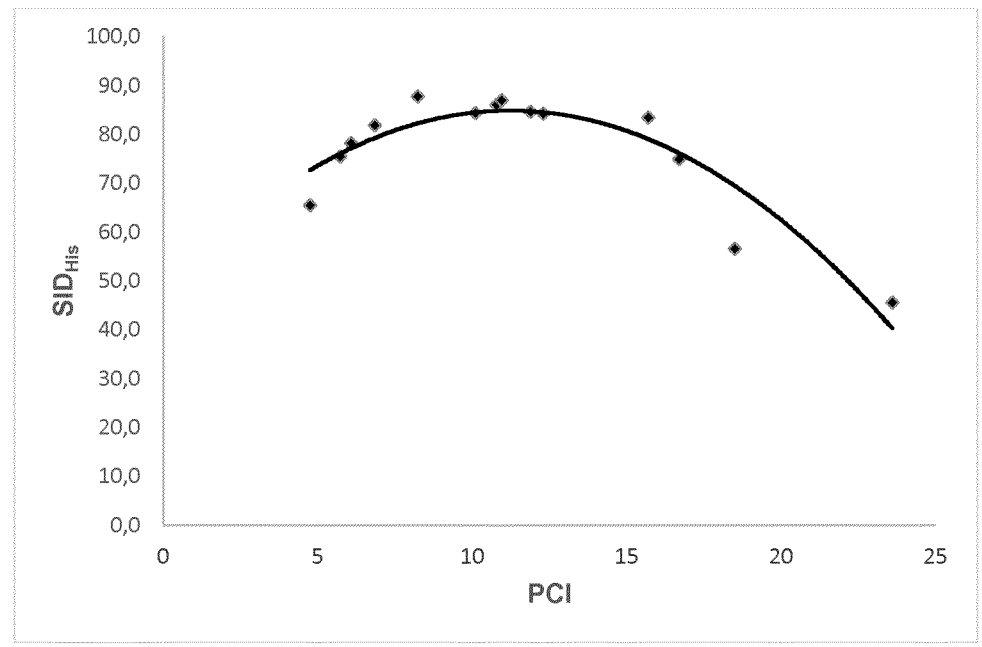
Fig. 23: Standardized ileal digestibility coefficent of histidine (SID$_{His}$) in full-fat soybeans for pigs (SID$_{His}$ = - 0.2915 $^\times$ PCI$^2$ + 6.548 $^\times$ PCI + 48.067)
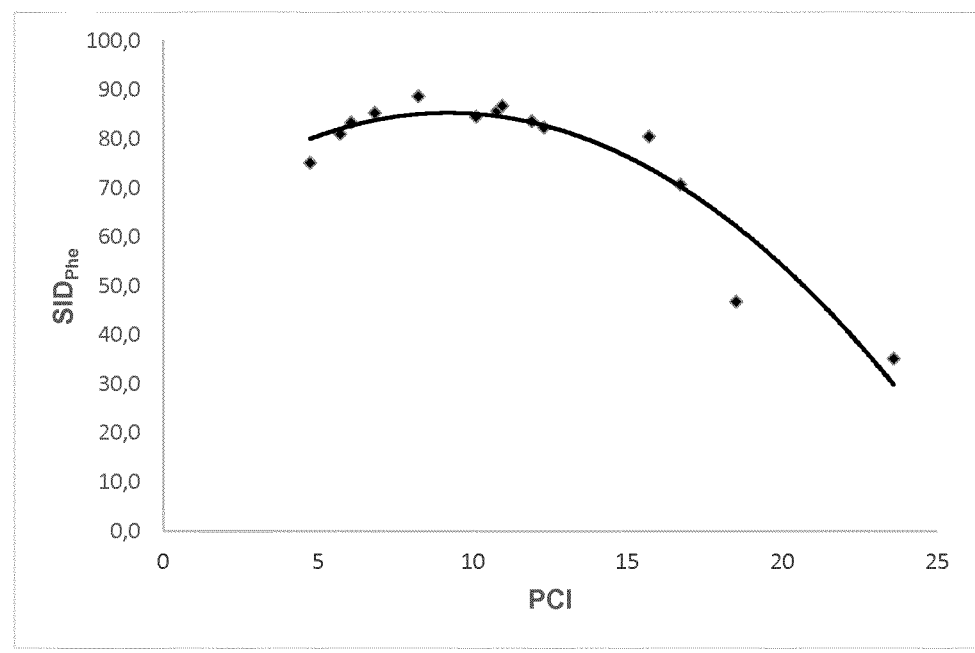
Fig. 24: Standardized ileal digestibility coefficent of phenylalanine (SID$_{Phe}$) in full-fat soybeans for pigs (SID$_{Phe}$ = - 0.2676 $^\times$ PCI$^2$ + 4.9292 $^\times$ PCI + 62.59)

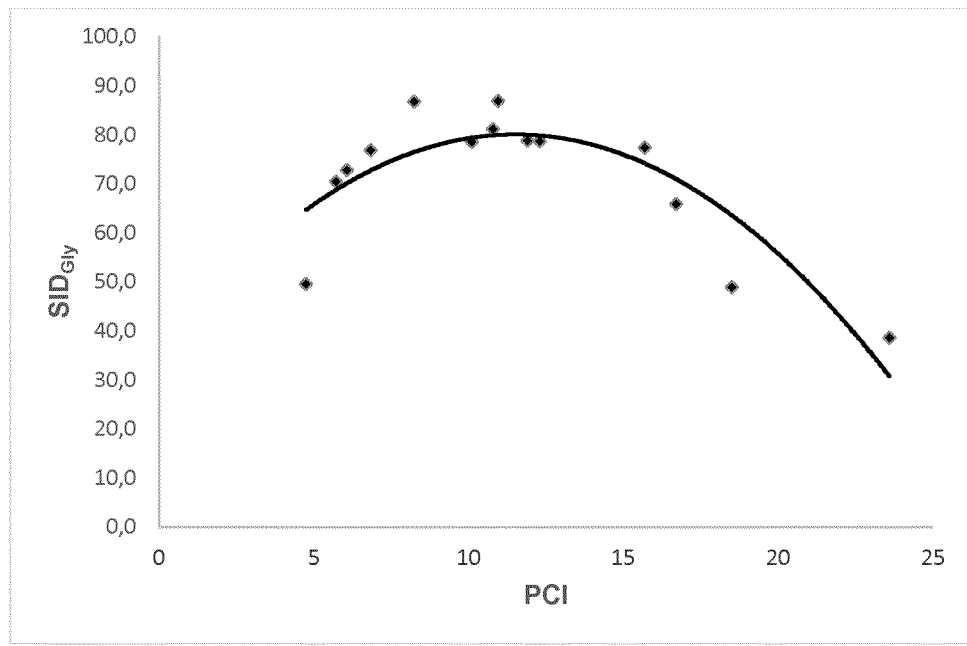
Fig. 25: Standardized ileal digestibility coefficent of glycine ($SID_{Gly}$) in full-fat soybeans for pigs ($SID_{Gly} = -0.3377 \times PCI^2 + 7.7741 \times PCI + 35.285$)
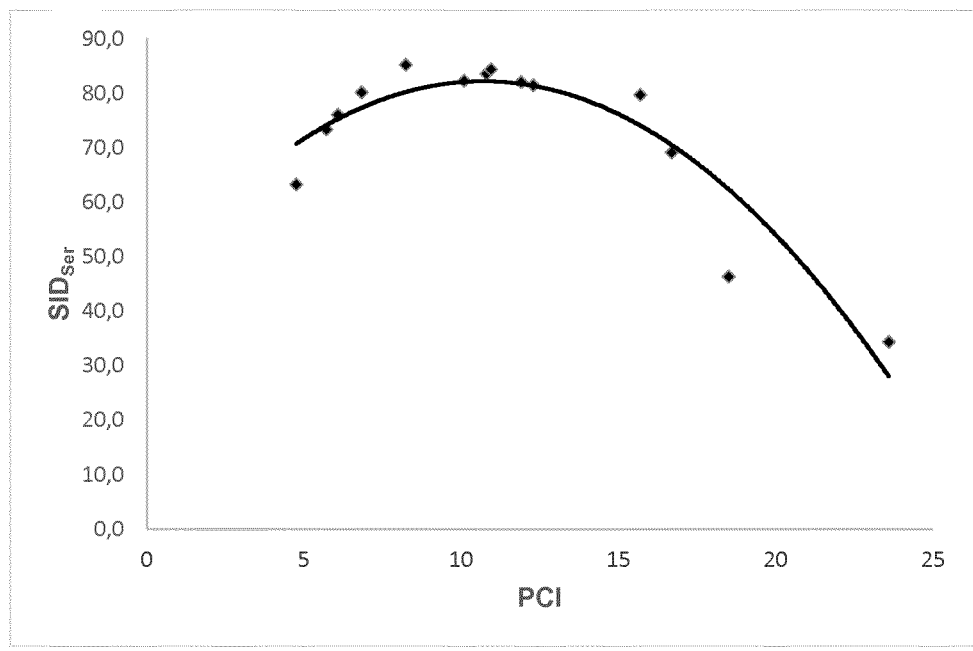
Fig. 26: Standardized ileal digestibility coefficent of serine ($SID_{Ser}$) in full-fat soybeans for pigs ($SID_{Ser} = -0.3257 \times PCI2 + 6.9689 \times PCI + 44.913$)

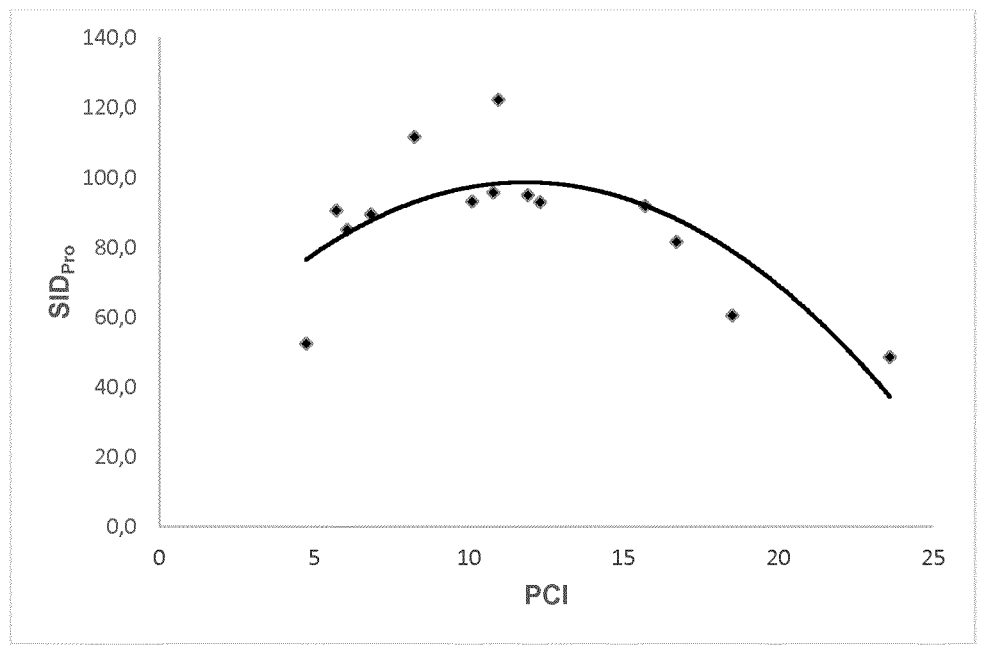
Fig. 27: Standardized ileal digestibility coefficent of proline ($SID_{Pro}$) in full-fat soybeans for pigs ($SID_{Pro} = -0.4428 \times PCI^2 + 10.473 \times PCI + 36.719$)
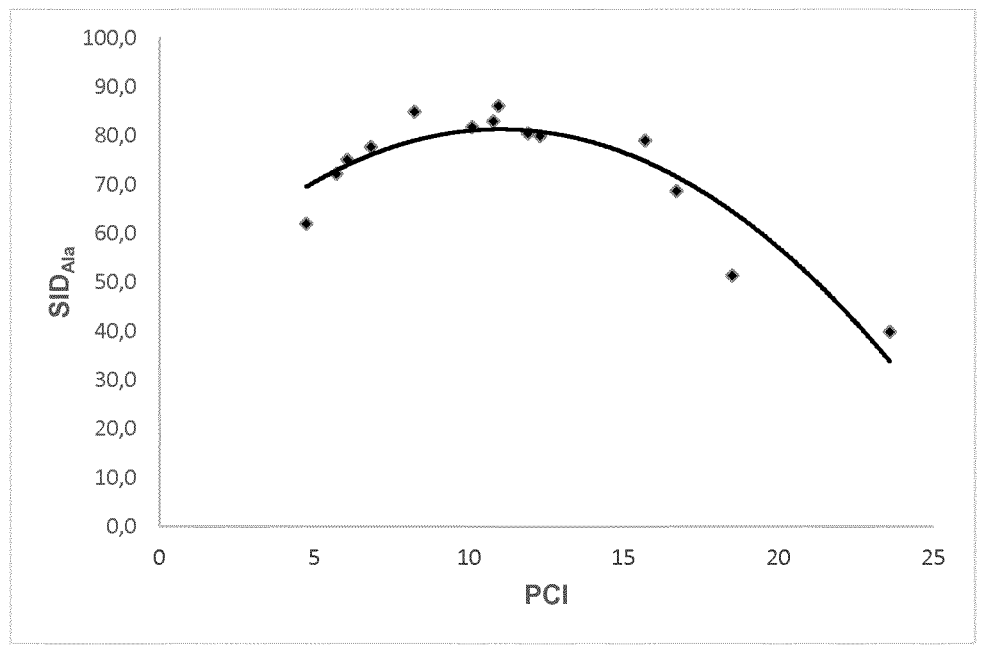
Fig. 28: Standardized ileal digestibility coefficent of alanine ($SID_{Ala}$) in full-fat soybeans for pigs ($SID_{Ala} = -0.3002 \times PCI^2 + 6.6179 \times PCI + 44.817$)

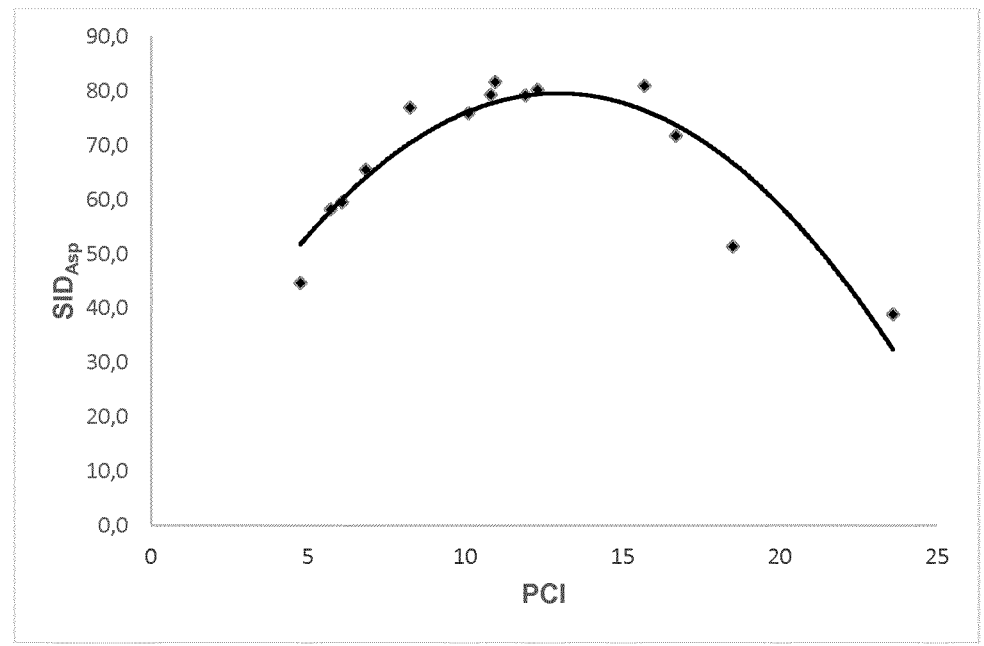
Fig. 29: Standardized ileal digestibility coefficent of aspartic acid ($SID_{Asp}$) in full-fat soybeans for pigs ($SID_{Asp} = -0.4159 \times PCI^2 + 10.756 \times PCI + 9.9347$)
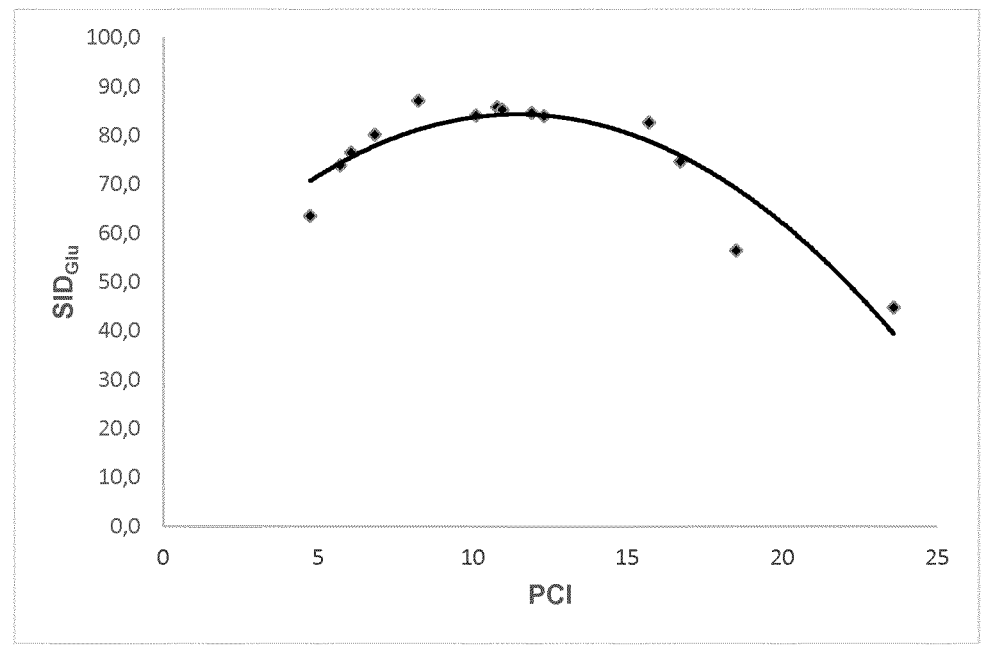
Fig. 30: Standardized ileal digestibility coefficent of glutamic acidne ($SID_{Glu}$) in full-fat soybeans for pigs ($SID_{Glu} = -0.3041 \times PCI^2 + 6.9635 \times PCI + 44.434$)

METHOD FOR THE DETERMINATION OF PROCESSING INFLUENCES ON THE NUTRITIONAL VALUE OF FEEDSTUFF RAW MATERIALS

The present invention relates to a method for the determination of processing influences on the nutritional value of feedstuff raw materials and/or feedstuffs, a process for the optimization of feedstuffs considering the determined processing influences and the thus obtained and/or obtainable feedstuffs.

Due to lot of reasons feedstuffs can have negative influences on animals and the respective animal products like meat and milk and in the worst case also on humans as their consumers. Examples for this are a wrong selection of the feedstuffs and the ration selection and the thus resulting nutrition and energy supply, a contamination of feedstuffs, a bioburden and/or toxin burden (mycotoxin) in spoiled feed and the so-called anti-nutritional factors in plant based feedstuffs.

Anti-nutritional factors result from the secondary metabolism of plants and are present only in particular plant species. They perform no essential functions in the primary metabolism. Rather, their function is the defense of varmints and pests, the regulation and function as dying stuffs and fragrances. The negative effects of anti-nutritional factors on the animal consist in the feed-uptake, a reduced animal performance, a change in digestibility of the nutrients, metabolic disorders and their toxicity.

Anti-nutritional factors can be grouped into the substance groups of carbohydrates, proteins, phenols and phenol derivatives, glucosides and glycosides, chelators and glucosinolates as well as goitrogens, whereby singular compounds can be grouped into more than one substance class.

Examples of anti-nutritional factors from the substance group of carbohydrates are:
The non-starch-polysaccharides, which are present as part of the cell walls, such as the pentosanes, which are present in lupines, barley, corn and rye, the beta-glucans, which are present in barley and rye, and the pectins, which are present in sunflowers. Due to their ability to swell these carbohydrates lead to the incorporation of water in animals, in particular in young poultry, an increase in the viscosity of the chymus, a decrease of energy density in the feedstuff, a decrease in the digestibility, and a decrease in growth and performance; and
indigestible oligosaccharides, for alpha-galactosides, such as the raffinose, stachyose, verbascose and ajugose, which are present in lupines, soybeans and rapeseed and which are quickly microbially converted in the caecum/colon, which leads to flatulences and diarrhea.

Examples of anti-nutritional factors from the substance group of proteins are:
Proteinase inhibitors, found in faba beans, peas, lupines, soy beans, guar and rice (used for (young) chicken, piglets and carnivores), which inhibit the activity of trypsin and chymotrypsin and thus lower the protein digestibility; and
the lectins (haem-agglutinins) found in phaesolus species (faba beans, peas, soy beans and lupines (used for monogastric animals) and which are bind to the receptors of the intestinal mucosa, which leads to resorption disorders and in vitro to a agglutination of red blood cells.

WO 2011/109624 A1 discloses soybeans possessing a genetic allele for the production of reduced trypsin inhibitor content in seeds. This document also discloses that progeny soybean plants of the ultra-low trypsin inhibitor soybeans, where the progeny comprises a combination of at least two soybean plants of traits of the WO 2011/109624 A1, so that said progeny soybean plant is not significantly different for said traits than soybean plants of the WO 2011/109624 A1 as determined at the 5% significance level when grown in the same environmental conditions.

Examples of anti-nutritional factors from the substance group of phenols and phenol derivatives are:
Tannins (phenol derivative), found in faba beans and peas (used for poultry, pigs and horses), which decrease the feed uptake, inhibit proteolytic enzymes, and decrease the protein digestibility, which results in constipations;
alkyl resorcinols, found in barley, often in triticale and very often in wheat, (used for monogastric animals), which lead to a depression in feed uptake and growth; and
gossypol, found in cottonseeds (used for all types of animals), which has a haemolytic effect because it binds to iron and leads to a discoloration of the yolk, disorders of the protein metabolism and the spermatogenesis as well as liver and kidney damages.

Examples of anti-nutritional factors from the substance group of glucosides and glycosides are:
Pyrimidine-glucosides (vicin, convicin etc.), found in faba beans and vetches (used for laying hens and sows), which lead to disorders of the fat metabolism, a reduced laying performance and hatchability and disorders of fertility and lactation;
alpha-galactosides, found in lupines, faba beans and peas;
cyanogenic glucosides, found in phaesolus species (vetches, flaxseed, tapioca and lupines) (used for horses and all types of livestock), which lead to symptoms of intoxication due to the release of prussic acid (respiratory poison); and
saponins, found in faba beans, peas and lupins (used for: (young) chicken), which give a bitter taste, which leads to a reduction in feed uptake, and have a haemolytic effect and are also an antagonist of vitamin D.

Examples of anti-nutritional factors from the substance group of alkaloids are:
The alkaloids spartein, lupinin, hydroxylupanin, angustifolin, solanin, found in lupines and in particular in tomatoes and potatoes (used for: monogastric animals, pigs and cattle), ergot alkaloids, found in particular in rye, which give a bitter taste, which leads to depression in feed uptake, but most notably alkaloids are toxic, the ergot alkaloids can lead to abortions, paralyzations and cramps, in the field of cattle alkaloids therefore lead to a decrease in the production of milk; and
sinapin, found in rapeseed (used for: laying hens, in particular brown egg layers), which the gut bacteria convert to trimethylamine (TMA), which is enriched in the liver when the TMA oxidase activity in the liver is not sufficiently high and gives a fishy smell of eggs.

Examples of anti-nutritional factors from the substance group of chelators are:
Phytic acid, found for example in corn, corn legumes and extractions shreds (used for: monogastric animals, pigs and poultry), which decrease the availability of two-charged ions such as $Ca^{2+}$, $Zn^{2+}$ and $Fe^{2+}$ in the organism by chelating these ions; and gossypol, found in cottonseeds (used for all types of animals), which has a haemolytic effect because it binds to iron and leads to a discoloration of the yolk, disorders of the protein metabolism and the spermatogenesis as well as liver and kidney damages.

Examples of anti-nutritional factors from the substance groups of glucosinolates are:

Glucobrassicin, gluconapin, glucobrassiconapin and progoitrin, all found in rapeseed (used for: breeding animals, in particular pigs, poultry and calves, dairy cows) are enzymatically cleaved under release of toxic isothiocyanate, thiocyanate and nitrile compounds; further glucosinolates and their cleavage products lead to a reduction in feed uptake, they interfere the fertility efficiency and the production of thyroid hormones, they promote the struma formation and cause the transition of goitrogens into the milk.

Also the goitrogens (found in soy beans, flaxseed and cabbage) lead to an enlargement of the thyroid gland (=struma).

The above non-limiting list of anti-nutritional factors and their negative effects on the animals illustrate that anti-nutritional factors have a big impact on the feeding praxis. Thus, in order to avoid the negative effects of anti-nutritional factors on the animal, anti-nutritional factors should be removed from the raw materials used for preparing feedstuffs. In case it is not possible to completely remove the anti-nutritional factors from the feedstuff raw materials, the supply of anti-nutritional factors to the animals must be limited, in order to avoid detrimental effects on the animals.

For the removal of anti-nutritional factors from the feedstuff raw materials or the reduction of their presence in feedstuff raw materials, the raw materials used preparing feedstuffs are subject to a processing in which they are subjected to heat treatment such as cooking or toasting which leads to a removal of amongst others proteinase inhibitors and lectins, or a treatment with alkali, which for example leads to a removal of sinapin. Therefore, many feedstuff raw materials are subjected to a heat treatment. In addition, feed products are also subjected to a heat treatment in order to remove moisture. For example, the article "Feed extrusion process description" by Galen J. Rokey et al. (Revista Brasileira de Zootecnia, vol. 39, pp. 510-518, 2010) discloses that extrusion cooking for the production of many products has come of ages within the past three decades and provides a very useful and economical tool for processing animal diets. This process permits better utilization of available cereal grains and vegetable and animal proteins to permit cost effective and nutritionally sound diets with improved and unique feeding characteristics. The articles further discloses that palatable, functional, and tailor-made feedstuffs can be profitably manufactured of raw material formulation, system configuration, and processing conditions.

However, such a heat-treatment can lead to a damage of the amino acids present in the feedstuff raw materials. For example, compounds with an amino group such as amino acids and proteins, are subjected to the Maillard reaction in the presence of reducing compounds, in particular of reducing sugars. This is in particular the case for lysine with an ε-amino group, which can react with a multitude of ingredients in feedstuff raw materials. The compounds resulting from these reactions can be partly absorbed in the intestine of the animal, but they do not have any nutritional value. For example, the free ε-amino group of lysine molecules or lysine containing proteins can react with the carbonyl group of reducing sugars, in particular of hexoses like glucose, in a reversible condensation reaction which initially gives a Schiff's base which subsequently is reacted in an irreversible Amadori rearrangement under formation of ε-N-desoxyketosyl lysine which is sometimes referred to as Amadori product or early Maillard product. The ε-N-desoxyketosyl lysine can further react under formation of brown pigments or melanoidines, which are yellow-brownish to almost black colored, nitrogen containing organic compounds. The Schiff's bases, at least those formed of aliphatic aldehydes and reducing sugars, can be absorbed almost completely in the intestine of mammals. By comparison, the metabolism of the Amadori product ε-N-desoxyketosyl is negligible. The conditions employed in the processing of feedstuff raw materials, in particular high temperatures in cooking or toasting, extreme pH values and high reactant concentrations, favor the Maillard reaction. However, a part of the reacted lysine derivatives are acid labile and can revert back to lysine during the acid hydrolysis step of the conventional wet chemical amino acid analysis. This does not, however, occur in the digestive tract. Consequently, the amino acid concentrations in the feedstuffs, determined by conventional amino acid analysis, will be misleading and will overestimate the real amino acid content and availability in the heat-damaged feedstuffs.

The Maillard reaction is considered the main reason for the degradation of amino acids and amino acid containing proteins in feedstuff raw materials, in particular of lysine or lysine containing proteins. However, apart from the Maillard reaction there are further reactions which lead to the degradation of amino acids and amino acid containing proteins. For example, the strong heating of proteins in the absence of fats or (reducing) sugars leads to the reaction of lysine molecules with the amino side chains of amino acids such as asparagine and glutamine under formation of internal peptide bonds, so-called isopeptides. Besides the reactions giving isopeptides other reactions also occur, such as the formation of lysino-alanine, the reaction of lysine molecules with oxidized polyphenols, the acylation of amino acids and the racemization of amino acids. In addition to the modification of lysine molecules, the processing of feedstuff raw materials also leads to the denaturation of proteins and the formation of extensive protein cross-linking, intra- as well as intermolecular, and also with other amino acids than lysine. The aforementioned reactions including the Maillard reaction can lead to a general loss of amino acids and reduction of the digestibility of the amino acids and proteins in the feedstuff raw materials and thus to a reduction of the uptake of amino acids, in particular lysine, and proteins.

A further processing of feedstuffs can also lead to a decrease in the availability or solubility of proteins. For example, U.S. Pat. No. 5,783,238 discloses a blended source of organic and inorganic nitrogen of variable solubilities in the form of non-protein nitrogen, peptides, amino acids and intact protein derived in the preferred embodiment of the feed additive of U.S. Pat. No. 5,783,238 from glutamic acid fermentation solubles and/or corn fermentation solubles to which a carrier, additional amino acids and enzymes can be added and which is superior to prior art compositions. This document further discloses that a normal chemical analysis of the feed additive based diets reflects a solubility value that would be obtained with non-processed materials because normal chemical analysis of feed ingredients is unable to distinguish modifications in rates of solubility. Chemically, modification in nitrogen solubility which occurs in the feed additive of U.S. Pat. No. 5,783,238 as a result of processing can be measured by measuring free chlorine. This analysis indicated that only 33% of the non-protein nitrogen components in the blend of U.S. Pat. No. 5,783,238 were readily soluble.

WO 97/02489 A1 and NZ 312221 A disclose a method for determining the reactive lysine digestibility co-efficient of a foodstuff. This method comprises the steps of a) introducing a marker into the foodstuff to be analyzed, b) feeding the foodstuff to a non-human subject for predetermined period of time, c) obtaining a sample of the foodstuff digest from the subject, d) determining the digestible reactive lysine content of the foodstuff by: i) introducing a lysine derivatizing agent into the foodstuff and ii) determining the digestible reactive lysine content of the foodstuff by measuring the equivalent derivatized lysine content in the foodstuff, e) determining the digestible reactive lysine content in the foodstuff digesta by i) introducing a lysine derivatizing agent for the epsilon-amino group of lysine, into the foodstuff digesta and ii) determining the digestible reactive lysine content of the foodstuff digesta by measuring the equivalent derivatized lysine content in the foodstuff digesta, f) measuring the marker concentration in both the foodstuff and foodstuff digesta, g) expressing the reactive lysine content of the both foodstuff and the foodstuff digesta per gram of the marker, and h) calculating the reactive lysine digestibility co-efficient.

Heat exposure is also of significant influence on the amino acid content of other feedstuffs, which are obtained from processes with high heat exposure, such as the so-called DDGS (dried distiller's grains with solubles). Typically, DDGS is obtained in plants for the preparation of bioethanol on the basis of starch containing cereals such as corn, wheat, barley and sorghum after distillation of the ethanol and drying of the remaining by-product stillage. The proteins, fibers and oils contained in the stillage are nutrients, which define its use as feedstuff. However, only the dried by-product is storable and can be also fed to other species than ruminants. Typically, the dried by-product is pelletized after drying and the thus obtained feedstuff is typically referred to as DDGS. About a third of the cereals used for bioethanol production result in DDGS. Each bushel of the cereals used in the bioethanol production (one U.S. bushel of cereals equals 35.2391 liters) gives about 2.7 gallons of ethanol (1 gallone equals 4.54609 liters), 18 pound of DDGS (1 pound equals 453.59237 g) and 18 pound of carbon dioxide. DDGS has a high content of residuals of cereal and residuals of yeast proteins, minerals and vitamins and thus, a high residual energy value. Due to its high protein content of about 30% and its additional energy value DDGS is a source of proteins and energy which can be easily digested by beef cattle and milking cows. Further, DDGS can be used for the feeding of poultry and pigs. The use of DDGS for feeding ruminants is particularly common and well documented in the USA. In North America about 80% of the DDGS volume is used for feeding cattle. However, the heat exposure in the distillation of the ethanol formed during the fermentation and in the drying of the remaining by-product leads to a strong heat stress on the amino acids in the by-product, which can lead to the Maillard reaction of amino acids and proteins, the formation of isopeptides and lysino-alanines, the reaction of amino acids with oxidized polyphenols, the acylation of amino acids, the racemization of amino acids, the denaturation of proteins and the formation of extensive protein cross linking.

Typically, the amounts of amino acids in a feedstuff raw material are either determined by use of standard methods of amino acid analysis or assessed by use of near-infrared spectroscopy. The standard methods for amino acid analysis are wet chemical methods, in which the amino acids present in the feedstuff raw materials are either first boiled in hydrochloric acid to set the amino acids free from the proteins to which they are mainly bound, followed by the chromatographic separation of the hydrolysate, or they are first oxidized, followed by the hydrolysis and finally the hydrolysate is subjected to a chromatographic separation. The first alternative is applicable to all amino acids with the exception of tryptophan, which is destroyed in the hydrolysis, and methionine and cystine, which are partially degraded by hydrolysis. However, the sulfur containing amino acids methionine, cystine and cysteine can be quantitatively determined if they are oxidized at 0° C. with performic acid to methionine sulfone and cysteic acid prior to the hydrolysis and if these derivatives are analyzed after the hydrolysis. Cystine and cysteine are both determined as cysteic acid in hydrolysates of an oxidized sample. During the hydrolysis the amino acids asparagine and glutamine are completely converted to aspartic and glutamic acid and can be determined as these. Therefore, glutamine and asparagine are always determined together with the naturally occurring glutamic acid and aspartic acid. Accordingly, the determined values for glutamic acid and aspartic acid are sum parameters. The second alternative is applicable to all amino acids with the exception of tyrosine, which however is degraded in the oxidation step. Both alternatives allow a precise determination of the amino acid contents. However, a big disadvantage is that both alternatives are very time-consuming and work-consuming. Therefore, these methods are not suitable for quick analyses, in particular not as routine methods. By comparison, near-infrared spectroscopy is not suitable for a precise, or even highly precise, determination of the amino acid contents in a sample. Rather, this method only allows to assess or predict the amino acid contents in a sample—this, however, very easy and very quick.

Evonik produces amino acids for feeds and has over 50 years experience in analyzing amino acids. In 2012 they tested around 15,000 samples a year via wet chemistry (see the article "Evonik's Amino NIR-NIR for the feed industry" by Richard Mills (http://nirperformance.com/2012/10/24/evoniks-amino-nir/). While wet chemistry reference methods remain the gold standard for analyzing amino acids, but rapid tests with NIR are increasingly important in delivering timely results to customers to help in the creation of the best possible diets. The NIR instruments are connected to a network, with the Evonik laboratory at the hub. This network is growing constantly and now includes around 870 NIR instruments located in feed mills and analytic laboratories around the world.

WO 01/15548 A1 and EP 1145645 A1 disclose a method of analyzing, selecting and enhancing raw materials for use in animal feed products in a manner which eliminates the systematic over formulation, whilst guaranteeing a desired level of nutrient in the supplemented product. In detail, these documents disclose a method comprising the steps of analyzing the nutritional composition of batches of raw material for use in an animal feed product comprising measuring the amount of at last amino acids in the raw material by near infrared reflectance spectroscopy, comparing the nutritional composition with a predetermined nutritional composition, calculating the amount of supplemental nutrients needed to bring the composition of the batch to the predetermined nutritional composition, determining a threshold value for which clusters of the raw material exist that are both economically and nutritionally favorable, screening the batches to reject those for which the amount of supplemental nutrients needed is greater than a threshold value and to accept those for which the amount of supplemental nutrients needed is less than a threshold value, and supplementing only the accepted batches of raw materials with the calculated amount of supplemental nutrients.

A multitude of parameters for the characterization of processing influences on feedstuff raw materials is known, but experiments have shown that none of the literature-known parameters is suitable for the adequate characterization of food-relevant processing influences on foodstuff raw materials. Amongst others this is due to the fact that the individual parameters lead to different statements. For example, the determination of the urease activity is the most common test to evaluate the quality of soybean processing. However, this test only allows to detect an under-processing of the feedstuff raw material but it is not suitable for detecting an over-processing of feedstuff raw materials, By comparison, the solubility of proteins of a sample in alkali in principle allows to distinguish over-processed products from adequately processed products. However, this distinction requires to make assumptions for the degree of heat damage at specific values for the solubility of proteins in alkali. Hence, the assumptions already have a big influence on the categorization of a feedstuff raw material and/or feedstuff. Furthermore, this method alone also leads to contradictory statements regarding the quality of a feedstuff raw material and/or feedstuff.

It is therefore not surprising that neither individual known parameters nor a specific combination of parameters has been yet accepted in the feedstuff industry as sufficient or even as mandatory for the characterization of food-relevant features.

Thus, there was a need for a method which permits the characterization of processing influences on the nutritional value of feedstuff raw materials on a global scale and independently from the specific significance and in particular, the strengths and weaknesses of the individual methods.

According to the present invention this problem is solved by obtaining a set of parameters which are complementary in their significance and thus are combinable. These parameters are amongst others the trypsin inhibitor activity, the urease activity, the protein solubility in alkali, the protein dispersibility index, and/or the ratio of the reactive amount of lysine to the total amount of lysine. A further parameter is at least one amino acid selected from the group consisting of methionine, cysteine, cystine, threonine, leucine, arginine, isoleucine, valine, histidine, phenylalanine, tyrosine, tryptophane, glycine, serine, proline, alanine, aspartic acid and glutamic acid. These parameters are obtained by quantitative analysis of a sample series of a feedstuff raw material from different time points of processing of the specific feedstuff raw material. For each of the determined parameters the so-called processing conditions indicator (PCI) is determined, which describes all conceivable processing conditions of a feedstuff raw material, i.e. under-, adequate or over-processing. The thus obtained processing conditions indicator is then plotted into a scale, to facilitate the categorization of a feedstuff raw material as under-processed, adequately processed or over-processed.

This procedure is not limited to any particular feedstuff raw material and thus can also be used for the determination of processing influences on feedstuffs, such as dried distiller's grains with solubles (DDGS).

An object of the present invention is therefore a method for the determination of processing influences on the nutritional value of a feedstuff raw material and/or feedstuff, comprising the steps of a) subjecting a sample of a processed feedstuff raw material and/or feedstuff to a1) a quantitative analysis of at least one parameter selected from the group consisting of trypsin inhibitor activity, urease activity, protein solubility in alkali and protein dispersibility index;

a2) a determination of the ratio of the reactive amount of lysine to the total amount of lysine comprising a quantitative analysis of the reactive amount of lysine and the total amount of lysine, followed by the formation of the ratio of the reactive amount of lysine to the total amount of lysine; and a3) a quantitative analysis of the amount of at least one amino acid selected from the group consisting of methionine, cysteine, cystine, threonine, leucine, arginine, isoleucine, valine, histidine, phenylalanine, tyrosine, tryptophan, glycine, serine, proline, alanine, aspartic acid and glutamic acid;

b) plotting the parameters obtained in steps a1) to a3) as a function of the time points of processing of the sample in step a);

c) determining the area in the plot of step b), where the value of the trypsin inhibitor activity, expressed as mg of trypsin per g sample, is more than 4, the increase in the pH value in the determination of the urease activity is more than 0.35, the value of the protein solubility in alkali, expressed as the percentage of protein in the sample that is soluble in an alkaline solution, is more than 85%, and/or the value of the protein dispersibility index, expressed as the percentage of the original nitrogen content of the sample, is more than 40%, and assigning the thus obtained area as under-processed;

d) determining the area in the plot of step b), where the value of the ratio of the reactive amount of lysine to the total amount of lysine is less than 90%, the value of the protein dispersibility index, expressed as the percentage of the original nitrogen content of the sample, is less than 15%, and/or the value of the protein solubility in alkali, expressed as the percentage of protein in the sample that is soluble in an alkaline solution, is less than 73%, and assigning the thus obtained area as over-processed;

e) determining the area in the plot of step b), where the value of the trypsin inhibitor activity, expressed as mg of trypsin per g sample, is less than 4, the value of the protein solubility in alkali, expressed as the percentage of protein in the sample that is soluble in an alkaline solution, is between 73 and 85%, the value of the protein dispersibility index, expressed as the percentage of the original nitrogen content of the sample, is between 15 and 40% and the value of the ratio of the reactive amount of lysine to the total amount of lysine is at least 90%, and assigning the thus obtained area as adequately processed;

and/or subtracting the areas determined in steps c) and d) from the plot of b) and assigning the thus obtained area as adequately processed;

f) generating a processing scale by standardizing the areas obtained in steps c) to e) to equal size, sorting them from over-processing to under-processing or vice versa and assigning a continuous scale to the standardized and sorted areas;

g) inserting the values of the parameters obtained in steps a1) to a3) into a power series, and forming the mean of the values obtained from each power series, wherein said mean is designated as the processing conditions indicator (PCI), and h) plotting the processing conditions indicator obtained in step g) into the processing scale obtained in step f) to indicate whether a feedstuff raw material and/or feedstuff is over-processed, adequately processed or under-processed.

In the context of the present invention the term the reactive amount of lysine is used to denote the amount of lysine, which is actually available for the animal, in particular for the digestion in the animal. By comparison, the term the total amount of lysine is used in the context of the present invention to the sum of the amount of lysine, which is actually available for the animal, in particular for the digestion in the animal, and of the amount of lysine, which is not available for the animal, in particular not for the digestion in the animal. The latter amount of lysine is typically due to degradation reactions of lysine, such as the already mentioned Maillard reaction.

In the context of the present invention a processing, which leads to damages on feedstuff raw materials and/or feedstuffs and in particular to decreased amounts of amino acids, is referred to as over-processing. By comparison, a processing, which does not give a complete or at least acceptable removal of anti-nutritional factors from feedstuff raw materials and/or feedstuff, is referred to as under-processing. Finally, a processing, which leads to a complete or at least acceptable destruction of anti-nutritional factors without a destruction of amino acids and/or proteins, is referred to as adequately-processing or adequate processing.

The quantitative analysis of the trypsin inhibitor activity is based on the ability of the inhibitors to form a complex with the enzyme trypsin and thus reduce its activity. Trypsin catalyzes the hydrolysis of the synthetic substrates N-alpha-benzoyl-D,L-arginine-p-nitroanilide (DL-BAPNA, IUPAC name N-[5-(diaminomethylideneamino)-1-(4-nitroanilino)-1-oxopentan-2-yl]benzylamide) and N-alpha-benzoyl-L-arginine-p-nitroanilide (L-BAPNA, IUPAC name N-[5-(diaminomethylideneamino)-1-(4-nitroanilino)-1-oxopentan-2-yl]benzylamide). This catalyzed hydrolysis releases the yellow-colored product p-nitroaniline free and thus, leads to a change in absorbance. The trypsin activity is proportional to the yellow color. The concentration of the p-nitroaniline can be determined by means of spectroscopy at a wavelength of 410 nm. L-BAPNA is typically used in the method ISO 14902 (2001) and DL-BAPNA is typically used in the method AACC 22.40-01 (a modification of method originally invented by Hamerstrand in 1981).

In the method ISO 14902 the sample is first finely ground with a 0.50 mm sieve. During the grinding any evolution of heat should be avoided. The ground sample is mixed with aqueous alkaline solution, e.g. 1 g of sample in 50 ml of sodium hydroxide solution (0.01 N), and the thus obtained solution, suspension, dispersion or emulsion is then stored for a period of up to ca. 24 hours at a temperature of 4° C. at the most. The thus obtained mixture has a pH of from 9 to 10, especially of from 9.4 to 9.6. The resulting solution is diluted with water and left standing. A sample of this solution, e.g. 1 ml, is taken and diluted as indicated by its presumed or previously approximated trypsin inhibitor activity content so that 1 ml of diluted solution would cause a 40 to 60% inhibition of the enzymatic reaction. Trypsin working solution, e.g. 1 ml, is added to a mixture of L-BAPNA, water and the diluted sample extract solution, e.g. 5 ml of L-BAPNA, 2 ml of (distilled) water and 1 ml of the appropriately diluted sample extract solution. The samples are then incubated for exactly 10 minutes at 37° C. The reaction is stopped by addition of 1 ml of acetic acid (30%). A blank sample is prepared as above, but the trypsin is added after the acetic acid. After centrifugation at 2.5 g, the absorbance is measured at a wavelength of 410 nm.

In the method AACC 22-40.01 the sample is first finely ground with a 0.15 mm sieve. During the grinding any evolution of heat should be avoided. The ground sample is mixed with aqueous alkaline solution, e.g. 1 g of sample in 50 ml of sodium hydroxide solution (0.01 N), and slowly stirred for 3 hours at 20° C. The pH of the thus obtained solution, suspension, dispersion or emulsion should be between 8 and 11, preferably between 8.4 and 10. The resulting solution, suspension, dispersion or emulsion is diluted with water, shaken and left standing. A sample of this solution, e.g. 1 ml, is taken and diluted as indicated by its presumed or previously approximated trypsin inhibitor activity content so that 1 ml of diluted solution would cause a 40 to 60% inhibition of the enzymatic reaction. Trypsin working solution, e.g. 2 ml, is added to a mixture of D,L-BAPNA, water and the diluted sample extract solution, e.g. 5 ml of D,L-BAPNA, 1 ml of (distilled) water and 1 ml of the appropriately diluted sample extract solution. The samples are then incubated for exactly 10 minutes at 37° C. The reaction is stopped by addition of 1 ml of acetic acid (30%). A blank sample is prepared as above, but the trypsin is added after the acetic acid. After centrifugation at 2.5 g, the absorbance is measured at a wavelength of 410 nm.

Independently from the method used, the trypsin inhibitor activity is calculated as mg trypsin inhibitor per g trypsin, with the following formula:

$$i = \frac{(Ar - Abr) - (As - \text{Abs})}{(Ar - Abr)}$$

i=inhibition percentage (%);
Ar=absorbance of the solution with standard;
Abr=absorbance of the blank with standard;
As=absorbance of the solution with sample;
Abs=absorbance of the blank with sample;

$$TIA = \frac{i}{100\%} \times \frac{m1 \times f1 \times f2}{m0}$$

TIA=trypsin inhibitor activity (mg/g);
i=inhibition percentage (%);
m0=mass of the test sample (g);
m1=mass of trypsin (g);
f1=dilution factor of the sample extract; and
f2=conversion factor based on the purity of trypsin.

One trypsin unit is defined as the amount of enzyme, which will increase the absorbance at 410 nm by 0.01 unit after 10 minutes of reaction for each 1 ml of reaction volume. Trypsin inhibitor activity is defined as the number of trypsin units inhibited (TUI). The TIU per ml is calculated using the formula $$TUI[\text{ml}] = \frac{A_{blank} - A_{sample}}{0.01 \times V_{dl.smp.}}$$

where
- $A_{blank}$=absorbance blank
- $A_{sample}$=absorbance sample
- $V_{dl.\ smp.}$=volume of the diluted sample solution in ml.

The thus obtained TUI is plotted against the volumes of the diluted sample solution, where the extrapolated value of the inhibitor volume to 0 ml gives the final TUI [ml]. Finally, the TUI per g sample is calculated with the formula TUI [g]=TUI [ml$^{-1}$]×d×50 where d=dilution factor (final volume divided by the amount taken).

The results of this analytical method should not exceed 10% of the average value for repeated samples.

The quantitative analysis of trypsin inhibitors activity therefore preferably comprises the steps
i) dissolving a sample of a feedstuff and/or feedstuff raw material in an alkali solution;
ii) diluting an aliquot of the solution obtained in step i) to provide a mixture in which the trypsin inhibitor concentration is sufficient for approximately 40 to 60% trypsin inhibition;
iii) adding a specific volume of a trypsin solution to the mixture obtained in step ii);
iv) adding BAPNA to the mixture obtained in step iii) to start the hydrolysis reaction of BAPNA with trypsin;
v) stopping the hydrolysis reaction;
vi) measuring the absorbance for the mixture obtained in step v) at a wavelength of 410 nm and calculating the number of trypsin units inhibited (TUI) with the formula $$TUI[\text{ml}] = \frac{A_{blank} - A_{sample}}{0.01 \times V_{dl.smp.}}$$

where
- $A_{blank}$=absorbance blank
- $A_{sample}$=absorbance sample
- $V_{dl.\ smp.}$=volume of the diluted sample solution in ml; and plotting the TUI obtained in step viii) against the volumes of the diluted sample solution, where the extrapolated value of the inhibitor volume to 0 ml gives the final TUI [ml]; and/or
vii) the TUI per g sample according to the formula TUI [g]=TUI [ml$^{-1}$]×d×50 where d=dilution factor (final volume divided by the amount taken).

The enzyme urease catalyzes the degradation of urea to ammonia and carbon dioxide. Since urease naturally occurs in soybeans, the quantitative analysis of this enzyme is the most common test to evaluate the quality of processed soybeans. Preferably, the quantitative analysis of urease is done according to the method of ISO 5506 (1988) or AOCS Ba 9-58. The method of AOCS Ba 9-58 determines the residual activity of urease as an indirect indicator to assess whether the protease inhibitors have been destroyed in the processing of a feedstuff raw material and/or feedstuff. Said residual activity of urease is measured as increase in the pH value in the test as consequence of the release of the alkaline compound ammonia into the media. The recommended level for said increase of the pH value is 0.01 to 0.35 unit rise (NOPA, 1997). A typical quantitative analysis of the urease activity of a feedstuff raw material and/or feedstuff is done like this: First, a solution of urea in a buffer comprising NaH$_2$PO$_4$ and KH$_2$PO$_4$ is prepared, e.g. 30 g of urea are added to 1 l of a buffer solution composed of 4.45 g of Na$_2$HPO$_4$ and 3.4 g KH$_2$PO$_4$ and the pH value of the thus obtained is measured. Subsequently, a sample of a feedstuff raw material and/or feedstuff, e.g. 0.2 g of a soybean sample, is added to this solution. A test tube or beaker with the thus obtained solution, suspension, dispersion, or emulsion is placed in a water bath, e.g. at a temperature of 30+/–5° C., preferably 30° C., for 20 to 40 minutes, preferably 30 minutes. Finally, the pH value of this solution, suspension, dispersion, or emulsion is measured, compared with the pH value of the original urea solution, and the difference is given as increase in pH.

The quantitative analysis of the urease activity therefore preferably comprises the steps of
i) preparing a solution of urea in a buffer comprising Na$_2$HPO$_4$ and KH$_2$PO$_4$;
ii) measuring the pH value of the solution of step i);
iii) adding a sample of a feedstuff raw material and/or feedstuff to the urea comprising solution;
iv) keeping the thus obtained solution, suspension, dispersion, or emulsion at a constant temperature for a certain time period, followed by measuring pH value of the solution, suspension, dispersion, or emulsion; and
v) expressing the difference between the pH values measured in steps ii) and iv) as increase in pH.

The solubility of proteins in alkali, hereinafter also referred to as the solubility of proteins in an alkaline solution or the alkali solubility of proteins, is an effective method to distinguish over-processed products from correctly-processed products, e.g. according to DIN EN ISO 14244.

The solubility of proteins in alkali or the alkali solubility of proteins comprises the determination of the percentage of protein that is solubilized in an alkali solution. Prior to the solubilization of the sample of a known weight of the feedstuff raw material and/or feedstuff, the nitrogen content of a sample with a specific weight is determined using a standard method for the determination of nitrogen, such as the Kjeldahl or Dumas method. The thus determined nitrogen content is referred to nitrogen content in total. Afterwards, a sample of the same weight and from the same source is suspended in an alkali solution of a defined concentration, preferably in an alkaline hydroxide solution, in particular in a potassium hydroxide solution. An aliquot of the thus obtained suspension is taken and centrifugated. Again, an aliquot of the thus obtained suspension is taken. The nitrogen content in this liquid fraction is determined using a standard method for the determination of nitrogen, such as the Kjeldahl or Dumas method. The thus determined nitrogen content is compared with the nitrogen content in total and expressed as the percentage of the original nitrogen content of the sample.

The quantitative analysis of the alkali solubility of proteins preferably comprises the steps of
i) determining the nitrogen content of a sample of a feedstuff raw material and/or feedstuff, preferably by a method such as the one according to Kjeldahl or Dumas;
ii) placing an aliquot of the sample of step i) in an alkali solution, preferably a solution of sodium hydroxide or potassium hydroxide, followed by stirring;
iii) centrifuging the suspension, solution, dispersion or emulsion obtained step ii);
iv) determining the nitrogen content in an aliquot of the solution or of the supernatant of the suspension, solution, dispersion or emulsion obtained from step iii) preferably by a method such as the one according to Kjeldahl or Dumas; and v) calculating the alkali solubility of proteins as the ratio of the nitrogen content determined in step iv) to the nitrogen content determined in step i).

Preferably, the alkaline solution used in step ii) has a pH value of from 11 to 14, in particular of from 12 to 13, for example 12.5. The amount of alkali, such as sodium hydroxide or potassium hydroxide, used for the preparation of the alkali solution depends on the volume of the solution to be prepared.

A typical alkali solution for the determination of the alkali solubility of proteins has a pH value of 12.5, for example, and a solution of potassium hydroxide with a concentration of 0.036 mol/l or 0.2% by weight. In step ii) 1.5 g of a soybean sample are for example placed in 75 ml of a potassium hydroxide solution, followed by stirring at 8500 rpm (rounds per minute) for 20 minutes at 20° C. Subsequently, an aliquot, for example about 50 ml, of the suspension, solution, dispersion or emulsion thus obtained are taken and immediately centrifugated at 2500 g for 15 min. Afterwards, an aliquot, for example 10 ml, of the supernatant of the suspension, solution, dispersion or emulsion thus obtained are taken and the content of nitrogen in said aliquot is determined by means of standard methods for the determination of nitrogen, such as the method of Kjeldahl or Dumas. Finally, the results are expressed as the percentage of the nitrogen content of the sample.

The determination of the protein dispersibility index (PDI) measures the solubility of proteins in water after blending a sample with water. This method also involves the determination of the nitrogen content in a sample of a known weight, which is typically done according to the same procedure as in the wet chemical analysis of proteins. The thus obtained nitrogen content is also referred to as the total nitrogen content. Further, the method also comprises the preparation of a suspension of a sample of the same weight as in the determination of the nitrogen content is suspended in water, which is typically done using a high-speed blender. The thus obtained suspension is filtered and the filtrate is subjected to a centrifugation. The nitrogen content in the thus obtained supernatant is determined by using again a standard method for the determination, such as the Kjeldahl or Dumas method, described above. The thus obtained nitrogen content is also referred to as the nitrogen content in solution. The protein dispersibility index is finally calculated as the ratio of the nitrogen content in solution to the total nitrogen content and expressed as the percentage of the original nitrogen content of the sample.

The quantitative analysis of the protein dispersibility index preferably comprises the steps of
i) determining the nitrogen content of a sample of a feedstuff raw material and/or feedstuff, preferably by a method such as the one according to Kjeldahl or Dumas;
ii) placing an aliquot of the sample of step i) in water;
iii) determining the nitrogen content in the dispersion obtained in step ii) preferably by a method such as the one according to Kjeldahl or Dumas; and
iv) calculating the protein dispersibility index as the ratio of the nitrogen content determined in step iii) to the nitrogen content determined in step i).

Since the values for the protein dispersiblity index increases with decreasing particle size, the results obtained in the determination of the protein dispersiblity index depend on the particle size of the sample. It is therefore preferred to grind the sample to be subjected to the determination of the protein dispersiblity index, in particular with a 1 mm mesh size.

The procedure described above is in accordance with the Official Method Ba 10-65 of the American Oil Chemists' Society (A.O.C.S.), according to which the determination of the protein dispersibility index is preferably performed. The nitrogen content of for example a soy sample is determined by means of standard methods for the determination of nitrogen, such as the method of Kjeldahl or Dumas. An aliquot, for example 20 g, of the soy sample is placed in a blender, and (de-ionized) water, for example 300 ml, are added at 25° C., followed by stirring, for example at 8500 rpm for 10 minutes. The thus obtained suspension, solution, dispersion or emulsion is filtered and the thus obtained solution, dispersion or emulsion is centrifugated, e.g. at 1000 g for 10 minutes. Finally, the nitrogen content in the supernatant is determined by means of standard methods for the determination of nitrogen, such as the method of Kjeldahl or Dumas.

Many feedstuffs are processed which leads to possible damages to the amino acids. This may render some of the amino acids unavailable for their use in nutrition. This is particularly the case for lysine, which has an ε-amino group that can react with the carbonyl group of other compounds, e.g. reducing sugars, present in the diet to give compounds that may be partially absorbed from the gut but which do not have any nutritional value to the animal. The reaction of the ε-amino group of free and/or protein-bound lysine with reducing sugars during heat treatment is known as the Maillard reaction. This reaction gives both early and late Maillard products. The early Maillard products are structurally altered lysine derivatives that are called Amadori compounds, while the late Maillard products are called melanoidins. The melanoidins do not interfer with the normal analysis for lysine and have no influence on the digestibility values that are calculated. They only result in lower concentrations of lysine being absorbed. Therefore, the melanoidins are typically not identified in the regular analysis of amino acid. By comparison, the Amadori compounds do interfer with the amino acid analysis and give inaccurate lysine concentrations for the sample being analyzed. The lysine being bound in these compounds is called "blocked lysine" and is biologically unavailable because it is resistant to any gastrointestinal enzymatic degradation.

The reactive lysine content in a sample can be determined using the Sanger reagent, i.e. 1-fluoro-2,4-dinitrobenzene (FNDB). The lysine determined by means of this method is therefore also referred to as FDNB-lysine. The Sanger reagent converts lysine to the yellow dinitrophenyl (DNP)-lysine, which can be extracted and measured spectrophotometrically at a wavelength of 435 nm or by high-performance liquid chromatography.

Alternatively, the reactive lysine content in a sample can be also determined with the guanidination reaction using the mild reagent O-methylisourea. In this method the O-methylisourea only reacts with the ε-amino group of lysine, but it does not react with the α-amino group of lysine. Therefore, the guanidination reaction can be used to determine free lysine and peptide-bound lysine. Preference is therefore given for the guanidation reaction for the determination of the reactive lysine. The guanidination reaction of lysine gives a homoarginine, which is further derivatized with ninhydrin and the resulting change in absorption can be measured at wavelength of 570 nm. Subsequently, the derivatized sample is hydrolyzed to give again the homoarginine. The determination of reactive lysine can also be done by means of the guanidation reaction of the undamaged protein-bound lysine in an alkaline medium to give homoarginine. In this type of reaction the guanidation is typically effected through the action of O-methylisourea (OMIU).

Since it is an easier method to use, preference is given to use the guanidation reaction for the determination of reactive lysine. The guanidation reaction involves the incubation of a sample of a feedstuff raw material and/or feedstuff in O-methylisourea. Preferably, the ratio of O-methylisourea to lysine is greater than 1000. The thus treated sample obtained from step i) is dried and analyzed for homoarginine, preferably by using ion exchange high performance liquid chromatography. Subsequently, said sample is derivatized with ninhydrin and the absorbance of the derivatized sample is measured at a wavelength of 570 nm. Afterwards, said sample is subjected to a hydrolysis, followed by the removal of the solvent to dryness of the sample. The weight and the molar quantity of honoarginine in the sample are determined. Finally, the amount of reactive lysine is calculated from the molar quantity of homoarginine.

The guanidation reaction for the determination of reactive lysine therefore preferably comprises the steps of
i) incubating a sample of a feedstuff raw material and/or feedstuff in O-methylisourea;
ii) analyzing the sample obtained from step i) for homoarginine;
iii) derivatizing the sample obtained from step ii) with ninhydrin;
iv) measuring the absorbance of the sample obtained from step iii) at a wavelength of 570 nm;
v) subjecting the sample from step iv) to a hydrolysis;
vi) determining the weight and the molar quantity of homoarginine in the hydrolyzed sample; and
vii) determining the amount of reactive lysine from the molar quantity of homoarginine obtained in step vi).

However, not only lysine is subject to heat damages in the processing of feedstuff raw materials and/or feedstuffs but also other amino acids. According to the method of the present invention, the amino acids methionine, cysteine, cystine, threonine, leucine, arginine, isoleucine, valine, histidine, phenylalanine, tyrosine, tryptophan, glycine, serine, proline, alanine, aspartic acid and glutamic acid are quantitatively analyzed in a sample of a feedstuff raw material and/or feedstuff. To a certain degree amino acids are not only present as single compounds but also as oligopeptides, e.g. dipeptides, tripeptide or higher peptides, formed in an equilibrium reaction from two, three or even more amino acids. The amino group of an amino acid is usually too weak as a nucleophile to react directly with the carboxyl group of another amino acid or it is present in protonated form ($-NH_3^+$). Therefore, the equilibrium of this reaction is usually on the left side under standard conditions. Notwithstanding, depending on the individual amino acids and the condition of a sample solution some of the amino acid to be determined may be not present as single compounds but to a certain degree as oligopeptides, e.g. dipeptide, tripeptide or higher peptide, formed of two, three or even more amino acids. Therefore, the sample of a feedstuff raw material and/or feedstuff should be subjected to a hydrolysis treatment, preferably an acidic or a basic hydrolysis, using for example hydrochloric acid or barium hydroxide. In order to facilitate the separation of the free amino acids and/or the identification and determination of the amino acids, the free amino acids are derivatized with a chromogenic reagent, if necessary. Suitable chromogenic reagents are known to the person skilled in the art. Subsequently, the free amino acids or the derivatized free amino acids are subjected to a chromatographic separation, in which the different amino acids are separated from each other because of the different retention times due to the different functional groups of the individual amino acids. Suitable chromatography columns, for example reversed phase columns, and suitable eluent solvent for the chromatographic separation of amino acids are known to the person skilled in the art. The separated amino acids are finally determined in the eluates from the chromatography step by comparison with a calibrated standard, prepared to the analysis. Typically, the amino acids, which are eluted from the chromatography column, are detected with a suitable detector, for example with a conductivity detector, a mass-specific detector or a fluorescence detector or a UV/VIS-detector depending when the amino acids were derivatized with a chromogenic reagent. This gives a chromatogram with peak areas and peak heights for the individual amino acids. The determination of the individual amino acids is performed by comparing the peak areas and peak heights with a calibrated standard or calibration curve for each amino acid. Since cystine ($HO_2C(-H_2N)CH-CH_2-S-S-CH_2-CH(NH_2)-CO_2H$) and cysteine ($HS-CH_2-CH(NH_2)-CO_2H$) are both determined as cysteic acid ($HO_3S-CH_2-CH(NH_2)-CO_2H$), the quantitative analysis does not make any distinction between the two amino acids. However, this does not appear to have any influence on the precision of the quantitative analysis because cysteine is typically very susceptible for oxidations and is therefore usually present as cystine.

The quantitative analysis of at least one amino acid other than reactive lysine preferably comprises the steps of:
i) placing a sample of a feedstuff raw material and/or feedstuff in an aqueous acidic solution;
ii) hydrolyzing the amino acids contained in said sample in order to set them free;
iii) optionally, derivatizing the free amino acids obtained in step ii) with a chromogenic reagent which enhances the separation and spectral properties of the amino acids;
iv) separating the free amino acids obtained in step ii) and/or iii) using column chromatography;
and
v) determining the amounts of the separated amino acids in the eluates obtained from step iv).

The procedure described above is in general used for the quantitative analysis of the total amount of lysine, which is required for the determination of the ratio of the reactive amount of lysine to the total amount of lysine, and for the quantitative analysis of at least one amino acid selected from the group consisting of methionine, cysteine, cystine, threonine, leucine, arginine, isoleucine, valine, histidine, phenylalanine, tyrosine, tryptophan, glycine, serine, proline, alanine, aspartic acid and glutamic acid.

The most critical point in the quantitative analysis of amino acids is the sample preparation, which differs with respect to the type of ingredients and the amino acids of major interests. Most of the amino acids can be hydrolyzed by a hydrolysis in hydrochloric acid (6 mol/l) for a time period of up to 24 hours. For the sulfur containing amino acids methionine, cysteine, and cystine the hydrolysis is preceded by an oxidation with performic acid. For the quantitative analysis of tryptophan the hydrolysis is performed with barium hydroxide (1.5 mol/l) for 20 hours.

Prior to the quantitative analysis of the amino acids, the sample of the feedstuff raw material and/or feedstuff is preferably finely grounded. During said grinding of the feedstuff raw material and/or feedstuff any evolution of heat should be avoided in order to avoid any further influence of heat on the contents of the feedstuff raw material and/or feedstuff, in particular with respect to the parameter which are subjected to the quantitative analysis of step a) of the method according to the present invention.

The values obtained for the parameters of the quantitative analysis performed in steps a1) to a3) according to the present invention are plotted in step b) of the method according to the present invention as a function of the time of processing of the samples which were subjected to the quantitative analysis.

In the following, in the step c) of the method according to the present invention the area in the plot of step b) is determined, where
- the value of the trypsin inhibitor activity, expressed as mg of trypsin per g sample, is more than 4,
- the increase in the pH value is more than 0.35,
- the value of the protein solubility in alkali, expressed as the percentage of protein in the sample that is soluble in an alkaline solution, is more than 85%, and/or
- the value of the protein dispersibility index, expressed as the percentage of the original nitrogen content in the sample, is more than 40%, and the areas in the plot of step b), where at least one of these provisions are given, are assigned as under-processed.

Next, in the step d) of the method according to the present invention the area in the plot of step b) is determined, where
- the value of the ratio of the reactive amount of lysine to the total amount of lysine is less than 90%,
- the value of the protein dispersibility index, expressed as the percentage of the original nitrogen content of the sample, is less than 15%, and/or
- the value of the protein solubility in alkali, expressed as the percentage of protein in the sample that is soluble in an alkaline solution, is less than 73%, and the areas in the plot of step b), where at least one of these provisions are given, are assigned as over-processed.

Finally, in the step e) of the method according to the present invention the area in the plot of step b) is determined, where
- the value of the trypsin inhibitor activity, expressed as mg of trypsin per g sample, is less than 4,
- the value of the protein solubility in alkali, expressed as the percentage of protein in the sample that is soluble in an alkaline solution, is between 73 and 85%,
- the value of the protein dispersibility index, expressed as the percentage of the nitrogen content of the sample, is between 15 and 40%, and
- the value of the ratio of the reactive amount of lysine to the total amount of lysine is at least 90%, and the areas in the plot of step b), where at least one of these provision are given, are assigned as adequately processed.

In addition or alternative, in the step e) of the method according to the present invention, the areas obtained in steps c) and d) are subtracted from the plot of step b) and the thus obtained area are assigned as adequately processed.

In the rare case where the performance of both alternatives in step e) gives different areas, the mean size is determined for these areas.

In order to facilitate a classification of the feedstuff raw material and/or the feedstuff subjected to the method according to the present invention as over-, under-, or adequately processed, it is further necessary to generate a processing scale, into which the processing conditions indicator of step f) is finally plotted. The size of the areas determined in steps c) to e) of the method according to the present invention may differ in their size, in particular with respect to their height (extension of the areas in the y-direction or along the ordinate) and/or their length (extension of the areas in the x-direction or along the abscissa). Therefore, in step f) of the method according to the present invention the areas determined in steps c) to e) are standardized to equal size and the standardized areas are subsequently sorted from over-processing to under-processing or vice versa. Further, a continuous scale is assigned to the standardized and sorted areas.

According to present invention the values of the parameters obtained in steps a1) to a3) of the method according to the present invention are inserted in step g) of the method according to the present invention into a power series and the thus obtained values are used to determine the mean value, which is the so-called processing conditions indicator (PCI).

A typical power series corresponds to the formula $$P(x) = \sum_{n=0}^{i}(a_{n,0} + a_{n,1} \times x_n + a_{n,2} \times x_n^2 + a_{n,3} \times x_n^3 + \ldots + a_{n,i} \times x_i^n)$$

with
i=maximum number of the analyzed parameters;
n=specific parameter;
$x_n$=value of a specific parameter; and
$a_n$=weighing factor for the parameter.

In the context of the present invention the weighing factor is preferably an integer. Preferably, the weighing factor is an integer from 1 to 10.

Considering the formation of the mean value for the values from the power series, the so-called processing conditions indicator (PCI) is obtained by means of the formula $$PCI = \frac{i}{(i+1)}\sum_{n=0}^{i}(a_{n,0} + a_{n,1} \times x_n + a_{n,2} \times x_n^2 + a_{n,3} \times x_n^3 + \ldots + a_{n,i} \times x_i^n)$$

with
i=maximum number of the analyzed parameters;
n=specific parameter;
$x_n$=value of a specific parameter; and
$a_n$=weighing factor for the parameter.

Finally, the processing conditions indicator obtained in step g) is then finally plotting in step h) of the method according to the present invention into the processing scale obtained in step f) to indicate whether the feedstuff raw material and/or feedstuff is over-processed, adequately-processed or under-processed.

Preferably, a series of samples of a processed feedstuff raw material and/or feedstuff from different time points of processing the same is subjected to the method according to the present invention in order to provide for a comprehensive sample population. Preferably, said series of sample comprises at least 100 samples, in particular 200, 300, 400, 500 or more samples. In case of a sample series the type of feedstuff raw material and/or feedstuff is preferably of the same type. Is further preferred to subjective more than one series of sample of preferably the same type of feedstuff raw material and/or feedstuff to the method according to the present invention. This has the advantage that also series of sample from different regions of the world can be subjected to the method according to the present invention. This allows to acquire a comprehensive data set, which also allows to determine the influence of processing influences on the nutritional value of a feedstuff raw material and/or feedstuff from different regions of the world. Thus, the method according to the present invention also considers the different climatic conditions in the various regions of the world, which together with the processing also have an influence on the nutritional value of feedstuff raw materials and/or feedstuffs.

Animal growth requires a dietary supply of amino acids. However, the amino acids present in feed are not completely digestible. Rather, the digestibility of an amino acid varies amongst the feedstuff raw materials or feedstuffs and further, it also varies amongst the amino acids. For example, the contents of anti-nutritive factors or of fibers in the matrix of the feedstuff raw material can decrease the digestibility of amino acids in an animal species. Amino acids are digested in the small intestine. Digestible amino acids are absorbed through the walls of the small intestine. Undigested materials pass along the large intestine and are excreted in the feces, at least theoretically. However, the microflora in the large intestine can metabolize some of the undigested amino acids for their own growth and development. As a consequence the absorption of amino acids in an animal species cannot be determined by a simple subtraction of the amino acids content in the feces from the amino acids content in the diet fed to the animal. To avoid the manipulation by hind-gut microbes, the digestibility of amino acids by monogastric animals is most correctly measured at the end of the small intestine. This part of the intestine is also called the ileum. Therefore, in the field of animal nutrition, the respective amino acid digestibility is also referred to as the ileal amino digestibility or the ileal digestibility coefficient. The ileal analysis method measures the difference between the amount of each of the amino acids in the diet and in the ileal digesta, divided by the amount of each of the amino acids in the diet. However, the digesta collected at the end of the small intestine contains large quantities of endogenous proteins and depending on the relative contribution of endogenous amino acid losses, the apparent ileal amino acid digestibility coefficients are effected to different extents. The expression apparent in context with the ileal amino acid digestibility therefore reflects the fact that the coefficients are not adjusted by the endogenous nitrogen and amino acid losses. The so-called apparent ileal amino acid digestibility coefficients or apparent ileal digestibility (AID) are calculated according the equation:

$$AID\ (\%) = \frac{AA_{intake} - AA_{excreted}}{AA_{intake}} \times 100$$

with
$AA_{intake}$=the amount of the individual amino acid, given to the animal as part of the diet, and
$AA_{excreted}$=the amount of the individual amino acid in ileal digesta.

The endogenous protein and amino acid losses can be separated into a basal (minimum) and an additional specific loss. The basal loss is non-specific and related to dry matter intake, whereas the specific loss is related to inherent factors in the feedstuffs, e.g. fiber and anti-nutritive factors such as trypsin-inhibitors, lectins and tannins. Endogenous secretions originate from various sources including saliva, pancreatic secretions, sloughed off epithelial cells and mucin. The amounts of basal endogenous protein and amino acid losses in ileal digesta can be determined by different methods. These methods include feeding protein-free diets, feedings diets containing protein sources that are assumed to be completely (100%) digestible with complete absorption of amino acids and the regression technique.

The imperfections of the apparent ileal digestibility are overcome when the apparent ileal digestibility coefficients are standardized by correcting them for basal endogenous amino acid losses. The thus obtained standardized or standard ileal digestibility coefficients are independent of the dietary amino acid level. The key issue for the determination of standardized ileal amino acid digestibility is the quantification of the level of the basal endogenous amino acid losses in digesta collected from the end of the small intestine. The standard ileal amino acid digestibility coefficients or standard(ized) ileal digestibility coefficients (SID) are calculated according to the equation:

$$SID\ (\%) = \left[\frac{AA_{intake} - (AA_{excreted} - AA_{bas.end.})}{AA_{intake}}\right] \times 100,$$

with
$AA_{intake}$=the amount of the individual amino acid, given to the animal as part of the diet,
$AA_{excreted}$=the amount of the individual amino acid in ileal digesta, and
$AA_{bas.end.}$=the amount of the basal endogenous amino acid loss.

Today, only one single standard digestibility coefficient of a specific amino acid in a feedstuff raw material and/or feedstuff for an animal species is used in practice for the evaluation of the nutritional value of said feedstuff raw material and/or feedstuff for an animal species, independently from the origin of the feedstuff raw material and/or feedstuff. Accordingly, the standard digestibility coefficients of today's practice do not consider any regional impacts on the nutritional value nor do they consider any impacts of the differences in the processing of the feedstuff raw material and/or feedstuff.

However, without the consideration of the additional influences on the nutritional value, today's practice of using one single standard digestibility coefficient does not allow to give a reliable and meaningful evaluation of the nutritional value of a feedstuff raw material and/or feedstuff.

By comparison, the method according to the present invention considers these influence because it correlates the standard ileal coefficient of an amino acid in a feedstuff raw material and/or feedstuff in animal species with the processing conditions indicator obtained for the same feedstuff raw material and/or feedstuff, which already reflects the influences of the processing on the nutritional value of the feedstuff raw material and/or feedstuff.

In one embodiment the method according to the present invention further comprises the steps of
i) determining the standardized ileal digestibility (SID) coefficient of an amino acid in a feedstuff raw material and/or feedstuff for an animal species by)
  i1) quantitative analysis of the amount of said amino acid (AA in the same sample as in step a);
  i2) administering said sample to an animal species and determining the endogenous loss of said amino acid ($AA_{basal,\ excret.}$) and the ileal amino acid outflow ($AA_{ileal,\ outflow}$); and i3) inserting the values of the parameters obtained in steps i1) and i2) into the general formula (II)

$$SID\ [\%] = \left[\frac{AA_{intake} - (AA_{ileal,outflow} - AA_{basal,excret.})}{AA_{intake}}\right] \times 100 \quad 5$$

and j) plotting the standardized ileal digestibility coefficient obtained in step i) as a function of the processing conditions indicator obtained in step g) and/or expressing said standard ileal digestibility coefficient in an equation as a function of the processing conditions indicator obtained in step g).

Examples for the calibration equations which give the ileal digestibility coefficient ($SID_{AA}$) as a function of the PCI are given below. These equations give the ileal digestibility coefficient for a specific amino acid in full-fat soybean in poultry or pigs:

Standardized ileal digestibility coefficient of methionine ($SID_{Met}$) of full-fat soybeans in poultry $SID_{Met} = -0.3581 \times PCI^2 + 8.679 \times PCI + 33.624$
$R^2 = 0.9399$, Standardized ileal digestibility coefficient of cystine ($SID_{Cys}$) of full-fat soybeans in poultry $SID_{Cystine} = -0.442 \times PCI^2 + 11.983 \times PCI - 13.905$
$R^2 = 0.9405$, Standardized ileal digestibility coefficient of methionine and cystine ($SID_{Met+Cystine}$) of full-fat soybeans in poultry $SID_{Met+Cystine} = -0.3861 \times PCI^2 + 9.8435 \times PCI + 13.53$
$R^2 = 0.9391$, Standardized ileal digestibility coefficient of lysine ($SID_{Lys}$) of full-fat soybeans in poultry $SID_{Lys} = -0.4187 \times PCI^2 + 11.462 \times PCI + 5.6474$
$R^2 = 0.9139$, Standardized ileal digestibility coefficient of threonine ($SID_{Thr}$) of full-fat soybeans in poultry $SID_{Thr} = -0.368 \times PCI^2 + 9.2054 \times PCI + 21.772$
$R^2 = 0.9469$, Standardized ileal digestibility coefficient of tryptophan ($SID_{Trp}$) of full-fat soybeans in poultry $SID_{Trp} = -0.4046 \times PCI^2 + 9.7674 \times PCI + 23.052$
$R^2 = 0.9431$, Standardized ileal digestibility coefficient of arginine ($SID_{Arg}$) of full-fat soybeans in poultry $SID_{Arg} = -0.3033 \times PCI^2 + 7.3008 \times PCI + 41.512$
$R^2 = 0.9494$, Standardized ileal digestibility coefficient of isoleucine ($SID_{Ile}$) of full-fat soybeans in poultry $SID_{Ile} = -0.3974 \times PCI^2 + 9.211 \times PCI + 29.802$
$R^2 = 0.9657$, Standardized ileal digestibility coefficient of leucine ($SID_{Leu}$) of full-fat soybeans in poultry $SID_{Leu} = -0.3639 \times PCI^2 + 8.3187 \times PCI + 35.843$
$R^2 = 0.9651$, Standardized ileal digestibility coefficient of valine ($SID_{Val}$) of full-fat soybeans in poultry $SID_{Val} = -0.388 \times PCI^2 + 9.0608 \times PCI + 29.464$
$R^2 = 0.9639$, Standardized ileal digestibility coefficient of histidine ($SID_{His}$) of full-fat soybeans in poultry $SID_{His} = -0.3554 \times PCI^2 + 9.1547 \times PCI + 25.938$
$R^2 = 0.9376$, Standardized ileal digestibility coefficient of phenylalanine ($SID_{Phe}$) of full-fat soybeans in poultry $SID_{Phe} = -0.3523 \times PCI^2 + 8.0374 \times PCI + 37.432$
$R^2 = 0.9719$, Standardized ileal digestibility coefficient of methionine ($SID_{Met}$) of full-fat soybeans in pigs $SID_{Met} = -0.3286 \times PCI^2 + 7.3561 \times PCI + 43.444$
$R^2 = 0.8625$, Standardized ileal digestibility coefficient of cystine ($SID_{Cys}$) of full-fat soybeans in pigs $SID_{Cys} = -0.4982 \times PCI^2 + 13.115 \times PCI - 11.392$
$R^2 = 0.7687$, Standardized ileal digestibility coefficent of methionine and cystine ($SID_{Met+Cystine}$) in full-fat soybeans for pigs $SID_{Met+Cystine} = -0.4237 \times PCI^2 + 10.534 \times PCI + 14.77$  $R^2 = 0.8026$, Standardized ileal digestibility coefficent of lysine ($SID_{Lys}$) in full-fat soybeans for pigs $SID_{Lys} = -0.4397 \times PCI^2 + 11.359 \times PCI + 11.75$
$R^2 = 0.8209$, Standardized ileal digestibility coefficent of threonine ($SID_{Thr}$) in full-fat soybeans for pigs $SID_{Thr} = -0.291 \times PCI^2 + 6.2769 \times PCI + 44.594$
$R^2 = 0.8414$, Standardized ileal digestibility coefficent of thryptophane ($SID_{Trp}$) in full-fat soybeans for pigs $SID_{Trp} = -0.3167 \times PCI^2 + 6.6559 \times PCI + 45.534$
$R^2 = 0.8544$, Standardized ileal digestibility coefficent of arginine ($SID_{Arg}$) in full-fat soybeans for pigs $SID_{Arg} = -0.261 \times PCI^2 + 5.3573 \times PCI + 63.685$
$R^2 = 0.8894$, Standardized ileal digestibility coefficent of isoleucine ($SID_{Ile}$) in full-fat soybeans for pigs $SID_{Ile} = -0.3204 \times PCI^2 + 6.7739 \times PCI + 48.135$
$R^2 = 0.8789$, Standardized ileal digestibility coefficent of leucine ($SID_{Leu}$) in full-fat soybeans for pigs $SID_{Leu} = -0.2901 \times PCI^2 + 5.7556 \times PCI + 55.925$
$R^2 = 0.8801$, Standardized ileal digestibility coefficent of valine ($SID_{Val}$) in full-fat soybeans for pigs $SID_{Val} = -0.2801 \times PCI^2 + 5.8136 \times PCI + 52.234$
$R^2 = 0.868$, Standardized ileal digestibility coefficent of histidine ($SID_{His}$) in full-fat soybeans for pigs $SID_{His} = -0.2915 \times PCI^2 + 6.548 \times PCI + 48.067$
$R^2 = 0.8501$, Standardized ileal digestibility coefficent of phenylalanine ($SID_{Phe}$) in full-fat soybeans for pigs $SID_{Phe} = -0.2676 \times PCI^2 + 4.9292 \times PCI + 62.59$
$R^2 = 0.8914$, Standardized ileal digestibility coefficent of glycine ($SID_{Gly}$) in full-fat soybeans for pigs $$SID_{Gly}=-0.3377\times PCI^2+7.7741\times PCI+35.285$$
$$R^2=0.7481,$$

Standardized ileal digestibility coefficent of serine ($SID_{Ser}$) in full-fat soybeans for pigs $$SID_{Ser}=-0.3257\times PCI^2+6.9689\times PCI+44.913$$
$$R^2=0.8601,$$

Standardized ileal digestibility coefficent of proline ($SID_{Pro}$) in full-fat soybeans for pigs $$SID_{Pro}=-0.4428\times PCI^2+10.473\times PCI+36.719$$
$$R^2=0.6098,$$

Standardized ileal digestibility coefficent of alanine ($SID_{Ala}$) in full-fat soybeans for pigs $$SID_{Ala}=-0.3002\times PCI^2+6.6179\times PCI+44.817$$
$$R^2=0.8469,$$

Standardized ileal digestibility coefficent of aspartic acid ($SID_{Asp}$) in full-fat soybeans for pigs $$SID_{Asp}=-0.4159\times PCI^2+10.765\times PCI+9.9347$$
$$R^2=0.8487,$$

and
Standardized ileal digestibility coefficent of glutamic acid ($SID_{Glu}$) in full-fat soybeans for pigs $$SID_{Glu}=-0.3041\times PCI^2+6.9635\times PCI+44.434$$
$$R^2=0.8545.$$

For each calibration the respective coefficient of determination, denoted as $R^2$, is given. In statistics, the coefficient of determination is a number that indicates how well data fit a statistical model—sometimes simply a line or curve. An $R^2$ of 1 indicates that the regression line fits well the data, while an $R^2$ of 0 indicates that the lines does not fit the data at all. In all cases the standardized ileal digestibility of the amino acids have an $R^2$ which is very close to 1. Accordingly, the statistical model fits the data very well.

The quantitative analysis of the steps a1) to a3) of the method according to the present invention is rather time and cost consuming. Near infrared measurements (NIR) of the respective feedstuff raw material and/or feedstuff would be a more time and cost efficient alternative for determining the influences of processing on the nutritional value of a feedstuff raw material and/or feedstuff. However, near infrared spectroscopy does not give the results with the desired precision; rather, it often leads to contradictory results. Accordingly, neither quantitative analysis nor near infrared spectroscopy alone are suitable for a cost and time efficient determination of processing influences on the nutritional value of a feedstuff raw material and/or feedstuff.

According to the present invention this problem is solved in that the near infrared absorptions obtained for a sample of a feedstuff raw material and/or feedstuff are correlated with the corresponding values of the quantitative analysis of the same. The thus obtained correlation of the values of the quantitative analysis with the absorptions of the NIR measurement is preferably depicted or plotted as a calibration graph, which facilitates the matching of the absorptions of the NIR measurements of other sample with the corresponding exact values for the parameters based on the quantitative analysis.

Another object of the present invention is therefore a method for the assessment of the processing influence on the nutritional value of a feedstuff raw material and/or feedstuff, comprising the steps of A) subjecting a sample of the same feedstuff raw material and/or feedstuff as in step a) of the method for the determination of the processing influence on the nutritional value of a feedstuff raw material and/or feedstuff to near-infrared (NIR) spectroscopy;

B) matching the absorption intensities at the respective wavelengths or wavenumbers in the NIR spectrum obtained in step A) with the corresponding parameters and their values determined in steps a1) to a3); and C) plotting the matching of step B) as a calibration graph and/or expressing the parameters determined in steps a1) to a3) in a calibration equation as a function of the absorption intensities at the respective wavelengths or wavenumbers matched in step B).

Depending on the spectrometer used, the near-infrared (NIR) spectra of step A) can be recorded at wavelengths between 400 and 2,500 nm with any suitable infrared spectroscopes working either on the monochromator principle or on the Fourier transform principle. Preferably, the NIR spectra are recorded between 1,000 and 2,500 nm. Wavelengths are easily converted into the respective wavenumbers and therefore, the NIR spectra can of course also be recorded at the corresponding wavenumbers. Since the organic compounds to be determined in the method according to the present invention, i.e. proteins and amino acids, are rich in 0-H bonds, C—H bonds and N—H bonds, they are suitable for the detection by means of near-infrared spectroscopy. However, a biological sample such as a feedstuff contains a multitude of different organic compounds and thus represents a complex matrix. Notwithstanding every biological substance has a unique near-infrared spectrum, comparable to an individual finger print. Consequently, two biological substances having exactly the same spectrum can be assumed to have the same physical and chemical composition and thus to be identical. On the other hand, if two biological substances have different spectra, it can be assumed that they are different, either in terms of their physical or chemical characteristics or in both terms. Due to their individual and highly specific absorption bands the signals of organic compounds and their intensities in NIR spectra can be easily attributed and correlated to a specific organic compound and its concentration in a sample of known weight. Thus, the NIR spectroscopy allows a reliable prediction or assessment of for example the amount of amino acids and proteins in a sample. Since the same sample of a specific feedstuff raw material and/or feedstuff is subjected to the quantitative analysis in step a) and to the NIR spectroscopy in step A), it is also possible to attribute and correlate absorptions and their intensities in an NIR spectrum to parameters, such as the trypsin inhibitor activity, urease activity, protein solubility in alkali and protein dispersibility index, and to their values and changes. Once, the absorption intensities at the respective wavelengths or wavenumbers have been successfully matched, i.e. attributed and correlated to the parameters of interest and their values, the NIR spectroscopy allows a reliable prediction or assessment of the influences of processing on the nutritional value of a feedstuff raw material and/or feedstuff. For this purpose a large number of NIR spectra, e.g. 100, 200, 300, 400, 500 or more, of a feedstuff raw material and/or feedstuff are recorded, and the absorption intensities at the respective wavelengths or wavenumbers are matched with the corresponding parameters and their values. When the sample of step A) is not translucent, the reflectance of the emitted light from the sample is measured and the difference between the emitted light and the reflected light is given as absorption. The thus obtained absorption intensities are used in the following steps, e.g. step B) above and, steps D) and G) below.

In one embodiment the method for the assessment of the processing influence on the nutritional value of a feedstuff raw material and/or feedstuff further comprises the steps of D) matching the absorption intensities at the respective wavelengths or wavenumbers in the NIR spectrum of a sample obtained in step B) with the processing conditions indicator obtained for the same sample in step g) of the method for the determination of the processing influence on the nutritional value of a feedstuff raw material and/or feedstuff; and E) plotting the matching of step D) as a calibration graph and/or expressing the processing conditions indicator in a calibration equation as a function of the absorption intensities at the respective wavelengths or wavenumbers matched in step D).

After completion of the NIR calibrations, NIR spectroscopy can be used as a routine method for assessing the processing influence on the nutritional value of a feedstuff raw material and/or feedstuff.

In a further embodiment the method for the assessment of the processing influences on the nutritional value of a feedstuff raw material and/or feedstuff further comprises the steps of F) subjecting a sample of a feedstuff raw material and/or feedstuff as in step a) of the method for the determination of the processing influence on the nutritional value of a feedstuff raw material and/or feedstuff to NIR spectroscopy;

G) reading off the values of at least one of the parameters of steps a1) to a3) matching to the absorptions in the NIR spectrum obtained in step F) from the calibration graph of step C), and/or inserting the absorption intensities at the respective wavelengths or wavenumbers in the NIR spectrum obtained in step F) into the calibration equation of step C) to obtain the values for the parameters of steps a1) to a3);

H) inserting the values for the parameters obtained in step G) into power series and forming the mean of the values obtained from each power series, wherein said mean is designated as the processing condition indicator (PCI); and/or I) reading off the PCI from the calibration graph of step E) and/or inserting the absorption intensities at the respective wavelengths or wavenumbers into the calibration equation of step E) to obtain the processing conditions indicator; and J) plotting the processing conditions indicator obtained in step H) and/or I) into the processing scale of the method for the determination of the processing influence on the nutritional value of a feedstuff raw material and/or feedstuff to indicate whether a feedstuff raw material and/or feedstuff is over-processed, adequately-processed or under-processed.

Preferably, in the step G) the same parameters as in the steps a1) to a3) are obtained.

Based on the calibrations already obtained for the processing conditions indicator and the specific digestibility coefficient, the method according to the present invention also allows to determine specific digestibility coefficient by means of NIR spectroscopy.

In another embodiment the method for the assessment of the processing influences on the nutritional value of a feedstuff raw material and/or feedstuff therefore further comprises the step of K) inserting the processing conditions indicator obtained in step H) into the calibration equation of step j) and/or reading off the functional value for the processing conditions indicator obtained in step I) to obtain a specific digestibility coefficient of an amino acid ($D_{AA}$) in the feedstuff raw material and/or feedstuff of step F).

Based on the data set and the respective calibrations obtained in the methods according to the present invention the method according to the present invention also allows to perform an assessment of the processing influences on the nutritional value of a feedstuff raw material and/or feedstuff from an unknown origin. Alternatively, the sample in step F) of the method for the assessment of the processing influences on the nutritional value of a feedstuff raw material and/or feedstuff is of the same origin as in step a) of the method for the determination of the processing influences on the nutritional value of a feedstuff raw material and/or feedstuff.

In one embodiment the sample used in step F) of the method for the assessment of the processing influences on the nutritional value of a feedstuff raw material and/or feedstuff is of unknown origin or is of the same origin as in step a) of the method for the determination of processing influences on the nutritional value of a feedstuff raw material and/or feedstuff.

For a feedstuff raw material and/or feedstuff which is considered over-processed the method also allows to determine the difference between the desired value and the real value of the content of an amino acid in a feedstuff raw material and/or feedstuff by comparing the maximum of the ileal digestibility coefficient of the amino acid of the feedstuff raw material and/or feedstuff in an animal species with the specific digestibility coefficient of the amino acid as obtained in the method according to the present invention for a specific sample.

The method for assessing the processing influences on the nutritional value of a feedstuff raw material and/or feedstuff according to the present invention therefore further comprises the step of L) determining the differential amount between the desired value and the real value for the amount of an amino acid in a feedstuff raw material and/or feedstuff from the difference between the maximum of the ileal digestibility coefficient of said amino acid of the method for the determination of the processing influences on the nutritional value of a feedstuff raw material and/or feedstuff and the specific digestibility coefficient of said amino acid obtained in step K).

By means of the specific digestibility coefficient ($D_{AA}$) obtained by the method according to the present matter for a specific amino acid in a specific sample of a feedstuff raw material and/or feedstuff it is also possible to determine the digestible amount of an amino acid in said sample. Said digestible amount of an amino acid can be simply obtained by multiplying the amount of an amino acid of a sample of a feedstuff raw material and/or feedstuff as obtained in step G) with the processing conditions indicator obtained in step K)

In a further embodiment the method for assessing the processing influences on the nutritional value of a feedstuff raw material and/or feedstuff according to the present invention therefore further comprises the step of M) determining the digestible amount of an amino acid in a sample of a feedstuff raw material and/or feedstuff by multiplying the amount of said amino acid in the sample of a feedstuff raw material and/or feedstuff obtained in step G) with the specific digestibility coefficient obtained in step K).

The feedstuff raw material and/or feedstuff which is used in the methods according to the present invention is preferably soy, soybeans, preferably full-fat soybeans, and/or soybean products, preferably soybean meal and soybean cake/expellers. This is because soy, soybeans and soybean products are the most relevant feedstuffs raw materials and/or feedstuffs.

In one embodiment of the methods according to the present invention the feedstuff raw material and/or feedstuff is soy, soybeans, or a soybean product.

The determination of the standard ileal digestibility coefficient and the specific digestibility coefficient obtained by the methods according to the present invention are not subject to any limitation regarding an animal species. Rather, these methods can be used for the determination and/or assessment of the standardized ileal digestibility coefficient and the specific digestibility coefficient for any conceivable animal species. Notwithstanding, preferred animal species in the context of the present invention are monogastric animals, i.e. animals having a single-chambered stomach, including omnivores such as pigs, poultry, e.g. turkeys and chicken, carnivores such as cats, and herbivores such as horses, deer and rabbits, and ruminants, such as cows, goats and sheep.

In one embodiment of the methods according to the present invention the animal species is an omnivore, carnivore, herbivore and/or ruminant.

The method according to the present invention can be carried on a computer. This allows to perform the method according to the present invention as a routine method. In this case the calibration equations obtained in steps C) and j) of the methods according to the present invention are stored on the computer, so that the computer only carries out the steps F) to J) and optionally the step K) of the method according to the present invention. Preferably, the computer also operates the near infrared spectrometer for step F) of the method. Additionally or alternatively, the computer carrying out the steps F) to J) and optionally the step K) of the method according to the present invention and the computer on which the calibration equations are stored are not identical. In this case, the first computer carrying out the steps F) to J) and optionally the step K) of the method according to the present invention and the second computer on which the calibration equation are stored form a network. Additionally or alternatively, the data set and the calibration curve are stored in a cloud to which the first computer has access and in this case the first computer and the cloud form a kind of network.

A further object of the present invention is therefore a computer-implemented process for determining the processing influences on the nutritional value of a feedstuff raw material and/or feedstuff, wherein the steps F) to J) are carried out by a computer and the calibration equations of step C) and/or of step E) are stored on the computer or a cloud.

In an embodiment the computer-implemented process according to the present invention further comprises that the additional steps K) and/or any of the steps L) and M) of the method according to the present invention are also carried out by the computer.

This has the advantage that the computer-implemented process does not only indicate if the examined feedstuff raw material and/or feedstuff is under-processed, adequately-processed or over-processed but it also indicates which quantities of a specific amino acid are required in order to provide an optimal diet for a specific animal species in case of an inadequately processed feedstuff raw material and/or feedstuff. This also allows to operate a plant for the preparation or mixing of feedstuffs by a computer.

A further object of the present invention is therefore also a process for the preparation of a feedstuff comprising the steps F) to L) of the method according to the present invention, wherein the process further comprises at least one of the steps N) further processing the feedstuff raw material and/or feedstuff, if the feedstuff raw material and/or feedstuff is indicated as under-processed, and/or O) supplementing the differential amount of an amino acid obtained according to step L) to the feedstuff raw material and/or feedstuff, if the feedstuff raw material and/or feedstuff is indicated as over-processed.

Said process facilitates the provision of feedstuffs which do not contain a critical amount of anti-nutritive factors, preferably less than 4 mg of trypsin inhibitors per g of feedstuff, and on the other hand contain the desired amount of amino acids for the animal species to which they are given. The desired amount of amino acids for the animal species is adjusted by means of the step N).

FIGURES

The FIGS. 1 to 12 show the ileal digestibility coefficients of amino acids ($SID_{AA}$) in full-fat soybeans for poultry as a function of the processing conditions indicator (the bracket term is the mathematical equation for the corresponding calibration equation). The diamonds in these figure (indicated as statistical series 1) correspond to the individual values for the PCIs of the respective processed full-fat soybeans and the straight line (indicated as polynominal) represents the graph of the function for the individual SID for the respective amino acid.

FIG. 1: Ileal digestibility coefficent of methionine in full-fat soybeans for poultry $(SID_{Met}=-0.3581 \times PCI^2+8.679 \times PCI+33.624)$ FIG. 2: Ileal digestibility coefficent of cystine in full-fat soybeans for poultry $(SID_{Cystine}=-0.442 \times PCI^2+11.983 \times PCI+13.905)$ FIG. 3: Ileal digestibility coefficent of methionine and cystine in full-fat soybeans for poultry $(SID_{Met+Cystine}=-0.3861 \times PCI^2+9.8435 \times PCI+13.53)$ FIG. 4: Ileal digestibility coefficent of lysine in full-fat soybeans for poultry $(SID_{Lys}=-0.4187 \times PCI^2+11.462 \times PCI+5.6474)$ FIG. 5: Ileal digestibility coefficent of threonine in full-fat soybeans for poultry $(SID_{Thr}=-0.368 \times PCI^2+9.2054 \times PCI+12.772)$ FIG. 6: Ileal digestibility coefficent of tryptophan in full-fat soybeans for poultry $(SID_{Trp}=-0.4046 \times PCI^2+9.7674 \times PCI+23.052)$ FIG. 7: Ileal digestibility coefficent of arginine in full-fat soybeans for poultry $(SID_{Arg}=-0.3033 \times PCI^2+7.3008 \times PCI+41.512)$ FIG. 8: Ileal digestibility coefficent of isoleucine in full-fat soybeans for poultry $(SID_{Ile}=-0.3974 \times PCI^2+9.211 \times PCI+29.802)$ FIG. 9: Ileal digestibility coefficent of leucine in full-fat soybeans for poultry $(D_{Leu}=-0.3639 \times PCI^2+8.3187 \times PCI+35.843)$ FIG. 10: Ileal digestibility coefficent of valine in full-fat soybeans for poultry $(SID_{Val}=-0.388 \times PCI^2+9.0608 \times PCI+29.464)$ FIG. 11: Ileal digestibility coefficent of histidine in full-fat soybeans for poultry $(SID_{His}=-0.3554 \times PCI^2+9.1547 \times PCI+25.938)$ FIG. 12: Ileal digestibility coefficent of phenylalanine in full-fat soybeans for poultry $(SID_{Phe}=-0.3523 \times PCI^2+8.0374 \times PCI+37.432)$ The FIGS. 13 to 30 show the ileal digestibility coefficients of amino acids ($SID_{AA}$) in full-fat soybeans for pigs as a function of the processing conditions indicator (the bracket term is the mathematical equation for the corresponding calibration equation). The diamonds in these figures (indicated as statistical series 1) correspond to the individual values for the PCIs of the respective processed full-fat soybeans and the straight line (indicated as polynominal) represents the graph of the function for the individual SID for the respective amino acid.

FIG. 13: Standard ileal digestibility coefficent of methionine ($SID_{Met}$) in full-fat soybeans for pigs $(SID_{Met}=-0.3286 \times PCI^2+7.3561 \times PCI+43.444)$ FIG. 14: Standard ileal digestibility coefficent of cystine ($SID_{Cys}$) in full-fat soybeans for pigs $(SID_{Cys}=-0.4982 \times PCI^2+13.115 \times PCI-11.392)$ FIG. 15: Standard ileal digestibility coefficent of lysine ($SID_{Met+Cystine}$) in full-fat soy beans for pigs $(SID_{Met+Cystine}=-0.4237 \times PCI2+10.534 \times PCI+14.77)$ FIG. 16: Standard ileal digestibility coefficent of lysine ($SID_{Lys}$) in full-fat soybeans for pigs $(SID_{Lys}=-0.4397 \times PCI^2+11.359 \times PCI+11.75)$ FIG. 17: Standard ileal digestibility coefficent of threonine ($SID_{Lys}$) in full-fat soybeans for pigs $(SID_{Trp}=-0.291 \times PCI^2+6.2769 \times PCI+44.594)$ FIG. 18: Standard ileal digestibility coefficent of thryptophan ($SID_{Trp}$) in full-fat soybeans for pigs $(SID_{Arg}=-0.3167 \times PCI^2+6.6559 \times PCI+45.534)$ FIG. 19: Standard ileal digestibility coefficent of arginine ($SID_{Arg}$) in full-fat soybeans for pigs $(SID_{Arg}=-0.261 \times PCI^2+5.3573 \times PCI+63.685)$ FIG. 20: Standard ileal digestibility coefficent of isoleucine ($SID_{Ile}$) in full-fat soybeans for pigs $(SID_{Ile}=-0.3204 \times PCI^2+6.7739 \times PCI+48.135)$ FIG. 21: Standard ileal digestibility coefficent of leucine ($SID_{Leu}$) in full-fat soybeans for pigs $(SID_{Leu}=-0.2901 \times PCI^2+5.7556 \times PCI+55.925)$ FIG. 22: Standard ileal digestibility coefficent of valine ($SID_{Val}$) in full-fat soybeans for pigs $(SID_{Val}=-0.2801 \times PCI^2+5.8136 \times PCI+52.234)$ FIG. 23: Standard ileal digestibility coefficent of histidine ($SID_{His}$) in full-fat soybeans for pigs $(SID_{His}=-0.2915 \times PCI^2+6.548 \times PCI+48.067)$ FIG. 24: Standard ileal digestibility coefficent of histidine ($SID_{Phe}$) in full-fat soybeans for pigs $(SID_{Phe}=-0.2676 \times PCI^2+4.9292 \times PCI+62.59)$ FIG. 25: Standard ileal digestibility coefficent of glycine ($SID_{Gly}$) in full-fat soybeans for pigs $(SID_{Gly}=-0.3377 \times PCI^2+7.7741 \times PCI+35.285)$ FIG. 26: Standard ileal digestibility coefficent of serine ($SID_{Ser}$) in full-fat soybeans for pigs $(SID_{Ser}=-0.3257 \times PCI2+6.9689 \times PCI+44.913)$ FIG. 27: Standard ileal digestibility coefficent of proline ($SID_{Pro}$) in full-fat soybeans for pigs $(SID_{Pro}=-0.4428 \times PCI^2+10.473 \times PCI+36.719)$ FIG. 28: Standard ileal digestibility coefficent of alanine ($SID_{Ala}$) in full-fat soybeans for pigs $(SID_{Ala}=-0.3002 \times PCI^2+6.6179 \times PCI+44.817)$ FIG. 29: Standard ileal digestibility coefficent of aspartic acid ($SID_{Asp}$) in full-fat soy beans for pigs $(SID_{Asp}=-0.4159 \times PCI^2+10.756 \times PCI+9.9347)$ FIG. 30: Standard ileal digestibility coefficent of glutamic acid ($SID_{Glu}$) in full-fat soy beans for pigs $(SID_{Glu}=-0.3041 \times PCI^2+6.9635 \times PCI+44.434)$

EXAMPLES

1. Determining the Processing Influences on the Nutritional Value of Full-Fat Soybeans and the Standardized Ileal Digestibility Coefficient of Amino Acids in Poultry Full-fat soybeans (FFSB) manufactured from a single batch were used to determine the effect of different heat treatment procedures on the nutritional composition and the standardized ileal digestibility (SID) of amino acids in poultry. Raw FFSB (K0) were subjected to a short time processing using wet heating at 80° C. for 1 minute (K1) or a long time processing at 100° C. for 6 minutes (K2) or at 100° C. for 16 minutes (K3), followed by further expanding at 115° C. for 15 seconds (K1/K2/K3-115) or at 125° C. for 15 seconds using an HL extruder OEE 15.2 from Amandus Kahl GmbH & Co. KG, Hamburg, Germany. Subsamples of K3 were further subjected to a heat treatment in an autoclave at 110° C. for 15 minutes (Z1), 30 minutes (Z2), 45 minutes (Z3), 60 minutes (Z4), 120 minutes (Z5), 180 minutes (Z6), 240 minutes (Z7), 300 minutes (Z8) or 360 minutes (Z9). Coming out of the expander the processed FFSB are transferred at a temperature of approximately 90° C. for 20 seconds to a dryer, where the FFSB are dried for 5 minutes with a temperature gradient from 85° C. to 40° C. After the drying stage the FFSB are allowed to cool to a temperature of 20° C. for 5 minutes.

The total amounts of the amino acids and the amount of reactive lysine in the different processed FFSB and the processing conditions indicator (PCI) of amino acids in poultry were determined using the method according to the present invention.

The different processed FFSB, the determined amounts of the individual amino acids and the processing conditions indicator (PCI) of amino acids in poultry are summarized in the table 1.

The standardized ileal digestibility (SID) for each amino acid in poultry as a function of the PCI are shown in the FIGS. 1 to 12.

The PCI of FFSB is compared with the curve of the SID for each amino acid of the FIGS. 1 to 12. This comparison shows that the PCIs of the FFSB indicated as Z1 or Z2 always a SID which is at the or at least close to the maximum of the individual curve. Thus, the FFSB indicated as Z1 or Z2 are considered as adequately-processed. By comparison, the FFSB indicated as K0, K1-115/125, K2-115/125 and K3-115/125 always have a SID which is right from the maximum of the individual curve and thus are considered as under-processed. Further, the SID of the FFSB indicated as Z3 to Z9 is always left from the maximum of the individual curve and thus are considered as over-processed.

A study of the standardized ileal digestibility coefficents of amino acids summarized in table 1 proves that the classification of the FFSB indicated as Z1 and Z2 as adequately-processed, of the FFSB indicated as K0, K1-115/125, K2-115/125 and K3-115/125 as under-processed and of the FFSB indicated as Z3 to Z9 as over-processed is correct because the FFSB indicated as Z1 and Z2 contain the highest digestibility coefficents. By comparison, all the other FFSB contain lower digestibility coefficents. This proves that the use of the PCI is a useful tool for the description of the influence of the processing conditions on the quality of the feedstuff raw material and/or feedstuff.

seconds to a dryer, where the FFSB are dried for 5 minutes with a temperature gradient from 85° C. to 40° C. After the drying stage the FFSB are allowed to cool to a temperature of 20° C. for 5 minutes. Another part of the raw FFSB (K0) were subjected to a heat treatment at 110° C. in an autoclave for 15 minutes (Z14) or for 30 minutes (Z15), or to a heat treatment at 150° C. in an autoclave for 3 minutes (Z16), 6 minutes (Z17), 9 minutes (Z18) or 12 minutes (Z19).

The total amounts of the amino acids and the amounts of reactive lysine in the differently processed FFSB and the processing conditions indicator (PCI) of amino acids in pigs were determined using the method according to the present invention.

The differently processed FFSB, the determined reactive amount of the individual amino acids and the processing conditions indicator (PCI) of amino acids in pigs are summarized in table 2.

The standardized ileal digestibility coefficient (SID) for each amino acid in pigs as a function of the PCI are shown in the FIGS. 13 to 30.

The PCI of FFSB is compared with the curve of the SID for each amino acid of the FIGS. 13 to 30. This comparison shows that the PCIs of the FFSB indicated as Z11 and Z12 always had an SID which is at the maximum or at least close

TABLE 1

Summary of the different processed FFSB, the determined standardized ileal digestibility coefficents of individual amino acids and the processing conditions indicator (PCI) in poultry.

| Processing | CP | Met | Cystine | Met + Cystine | Lys | Thr | Trp | Arg | Ile | Leu | Val | His | Phe | PCI |
| --- | --- | --- | --- | --- | --- | --- | --- | --- | --- | --- | --- | --- | --- | --- |
| K0 | 40 | 43 | 28 | 35 | 49 | 38 | 32 | 47 | 29 | 32 | 30 | 48 | 33 | 23.6 |
| K1-115 | 58 | 56 | 39 | 47 | 63 | 52 | 47 | 65 | 48 | 51 | 49 | 62 | 53 | 20.4 |
| K1-125 | 69 | 75 | 59 | 67 | 74 | 68 | 70 | 73 | 67 | 68 | 67 | 75 | 68 | 18.5 |
| K2-115 | 71 | 77 | 61 | 69 | 75 | 71 | 73 | 75 | 70 | 71 | 70 | 76 | 70 | 17.1 |
| K2-125 | 75 | 78 | 61 | 69 | 79 | 72 | 70 | 81 | 72 | 73 | 72 | 79 | 74 | 16.7 |
| K3-115 | 70 | 76 | 62 | 69 | 75 | 70 | 71 | 75 | 70 | 70 | 69 | 76 | 70 | 16.8 |
| K3-125 | 76 | 81 | 64 | 72 | 81 | 75 | 77 | 80 | 77 | 77 | 76 | 81 | 77 | 15.7 |
| Z1 | 81 | 85 | 68 | 76 | 84 | 80 | 82 | 85 | 82 | 82 | 81 | 85 | 82 | 12.3 |
| Z2 | 82 | 87 | 67 | 77 | 85 | 80 | 83 | 86 | 84 | 84 | 83 | 86 | 84 | 11.9 |
| Z3 | 79 | 85 | 63 | 74 | 82 | 77 | 80 | 85 | 82 | 82 | 81 | 84 | 82 | 10.8 |
| Z4 | 80 | 85 | 65 | 75 | 82 | 78 | 81 | 85 | 83 | 83 | 82 | 84 | 82 | 10.1 |
| Z5 | 78 | 85 | 58 | 72 | 78 | 77 | 81 | 86 | 83 | 84 | 82 | 82 | 84 | 8.7 |
| Z6 | 74 | 82 | 52 | 68 | 71 | 74 | 77 | 82 | 80 | 82 | 80 | 77 | 81 | 7.2 |
| Z7 | 67 | 74 | 46 | 61 | 62 | 66 | 69 | 76 | 73 | 75 | 72 | 71 | 75 | 6.5 |
| Z8 | 64 | 71 | 40 | 57 | 57 | 61 | 65 | 73 | 69 | 71 | 68 | 65 | 72 | 5.4 |
| Z9 | 52 | 60 | 25 | 44 | 40 | 50 | 53 | 63 | 58 | 61 | 57 | 54 | 62 | 4.5 |

2. Determining the Processing Influences on the Nutritional Value of Full Fat Soy Beans and the Standard Ileal Digestibility Coefficient of Amino Acids in Pigs Full-fat soybeans (FFSB) manufactured from a single batch were used to determine the effect of different heat treatment procedures on the nutritional composition and the standardized ileal digestibility (SID) of amino acids in pigs. Raw FFSB (K0) were subjected to a short time processing using wet heat at 80° C. for 1 minute followed by further expanding at 125° C. for ca. 15 seconds (K4), a long time processing at 100° C. for 6 minutes followed by further expanding at 125° C. for ca. 15 seconds (K5), or a long time processing at 100° C. for 16 minutes followed by further expanding at 125° C. for ca. 15 seconds (K6), using an extruder OEE 15.2 from Amandus Kahl GmbH & Co. KG, Hamburg, Germany. Subsamples of K6 were further processed in an autoclave at 110° C. for 15 minutes (Z10), 30 minutes (Z11), 45 minutes (Z12), and 60 minutes (Z13). Coming out of the expander the processed FFSB are transferred at a temperature of approximately 90° C. for 20 to the maximum of the individual curve. Thus, the FFSB indicated as Z11 to 12 are considered as adequately-processed. By comparison, the FFSB indicated as K0, and K4 to K6 always have an SID which is right from the maximum of the individual curve, and thus they are considered as under-processed. Further, the SID of the FFSB indicated as Z13 to 19 is always left from the maximum of the individual curve and thus they are considered over-processed.

A study of the standardized ileal digestibility coefficients of amino acids summarized in table 2 proves that the classification of the FFSB indicated as Z11 and Z12 as adequately-processed, of the FFSB indicated as K0 and K4 to K6 as under-processed and of the FFSB indicated as Z13 to Z19 as over-processed is correct because the FFSB indicated as Z11 and Z12 contain the highest digestibility coefficients of the amino acids. By comparison, all the other FFSB contain lower digestibility coefficents of amino acids. This proves that the use of the PCI is a useful tool for the description of the influence of the processing conditions on the quality of the feedstuff raw material and/or feedstuff.

TABLE 2

Summary of the different processed FFSB, the determined standardized ileal digestibility coefficients of individual amino acids and the processing conditions indicator (PCI) in pigs.

| Processing | CP | Met | Cystine | Met + Cystine | Lys | Thr | Trp | Arg | Ile | Leu | Val | His | Phe | Gly | Ser | Pro | Ala | Asp | Glu | PCI |
|---|---|---|---|---|---|---|---|---|---|---|---|---|---|---|---|---|---|---|---|---|
| K0 | 41.7 | 40.0 | 30.1 | 35.3 | 42.3 | 36.7 | 32.9 | 49.5 | 35.4 | 36.0 | 39.0 | 45.6 | 35.2 | 38.5 | 34.4 | 48.5 | 39.9 | 38.9 | 44.8 | 23.6 |
| K4 | 52.4 | 52.6 | 41.4 | 47.4 | 57.4 | 47.2 | 43.8 | 61.3 | 48.3 | 47.2 | 49.8 | 56.6 | 46.8 | 48.9 | 46.4 | 60.5 | 51.3 | 51.4 | 56.5 | 18.5 |
| K5 | 70.2 | 73.6 | 65.3 | 70.2 | 74.8 | 66.0 | 66.2 | 79.7 | 70.9 | 70.9 | 69.8 | 74.9 | 70.7 | 65.9 | 69.2 | 81.6 | 68.6 | 71.7 | 74.7 | 16.7 |
| K6 | 80.5 | 82.6 | 75.2 | 79.8 | 84.0 | 76.1 | 78.1 | 87.9 | 81.5 | 81.0 | 80.1 | 83.4 | 80.6 | 77.4 | 79.7 | 91.8 | 78.9 | 81.0 | 82.7 | 15.7 |
| Z10 | 81.3 | 84.2 | 74.8 | 80.4 | 83.7 | 77.6 | 80.1 | 89.7 | 83.1 | 83.0 | 81.3 | 84.2 | 82.4 | 78.6 | 81.5 | 93.0 | 79.9 | 80.2 | 83.9 | 12.3 |
| Z11 | 81.8 | 84.3 | 72.5 | 79.1 | 83.9 | 77.7 | 80.7 | 91.0 | 83.8 | 83.9 | 81.6 | 84.6 | 83.6 | 78.8 | 82.1 | 94.9 | 80.4 | 79.2 | 84.7 | 11.9 |
| Z12 | 83.2 | 86.9 | 73.8 | 81.1 | 84.9 | 79.7 | 82.6 | 92.1 | 86.3 | 86.3 | 84.3 | 86.1 | 85.8 | 81.1 | 83.6 | 95.8 | 82.9 | 79.3 | 85.7 | 10.8 |
| Z13 | 81.4 | 85.9 | 69.1 | 78.1 | 82.0 | 78.5 | 81.4 | 91.3 | 85.6 | 85.6 | 83.1 | 84.3 | 84.6 | 78.5 | 82.3 | 93.1 | 81.8 | 75.9 | 84.1 | 10.1 |
| Z14 | 87.4 | 85.3 | 77.7 | 82.4 | 88.2 | 81.4 | 81.6 | 93.2 | 84.5 | 85.2 | 83.9 | 87.0 | 86.8 | 86.8 | 84.5 | 122.3 | 86.0 | 81.7 | 85.2 | 10.9 |
| Z15 | 86.3 | 86.7 | 77.3 | 82.9 | 86.4 | 82.8 | 83.5 | 93.9 | 85.6 | 86.6 | 85.3 | 87.7 | 88.7 | 86.7 | 85.3 | 111.7 | 84.9 | 76.9 | 87.1 | 8.2 |
| Z16 | 77.4 | 81.1 | 61.6 | 71.8 | 73.2 | 77.3 | 79.0 | 89.3 | 81.0 | 83.2 | 80.9 | 81.9 | 85.4 | 76.8 | 80.2 | 89.4 | 77.7 | 65.5 | 80.2 | 6.8 |
| Z17 | 72.6 | 76.7 | 50.8 | 63.9 | 65.9 | 73.0 | 74.9 | 87.9 | 78.4 | 81.0 | 78.3 | 78.2 | 83.4 | 72.8 | 76.1 | 85.1 | 75.0 | 59.5 | 76.5 | 6.08 |
| Z18 | 68.9 | 74.0 | 45.7 | 59.9 | 60.5 | 70.0 | 73.0 | 85.2 | 75.3 | 78.2 | 75.3 | 75.4 | 81.0 | 70.4 | 73.4 | 90.5 | 72.2 | 58.2 | 73.8 | 5.73 |
| Z19 | 57.6 | 63.9 | 25.0 | 44.0 | 44.4 | 59.8 | 62.4 | 77.9 | 67.6 | 71.8 | 67.5 | 65.5 | 75.2 | 49.5 | 63.6 | 52.4 | 61.9 | 44.6 | 63.5 | 4.76 |

The invention claimed is:

1. A method for determining processing influences on nutritional value of a feedstuff raw material and/or feedstuff, the method comprising
   a) subjecting a sample of a processed feedstuff raw material and/or feedstuff to
      a1) a quantitative analysis of at least one parameter selected from the group consisting of trypsin inhibitor activity, urease activity, protein solubility in alkali and protein dispersibility index;
      a2) a determination of a ratio of a reactive amount of lysine to a total amount of lysine comprising a quantitative analysis of the reactive amount of lysine and the total amount of lysine, followed by a formation of the ratio of the reactive amount of lysine to the total amount of lysine; and
      a3) a quantitative analysis of an amount of at least one amino acid selected from the group consisting of methionine, cysteine, cystine, threonine, leucine, arginine, isoleucine, valine, histidine, phenylalanine, tyrosine, tryptophan, glycine, serine, proline, alanine, aspartic acid and glutamic acid;
   b) plotting parameters obtained in a1) to a3) as a function of time points of processing of the sample in a);
   c) determining an area in the plot obtained in b), where a value of the trypsin inhibitor activity, expressed as mg of trypsin per g sample, is more than 4, an increase in pH value in determining the urease activity is more than 0.35, a value of the protein solubility in alkali, expressed as a percentage of protein in the sample that is soluble in an alkaline solution, is more than 85%, and/or a value of the protein dispersibility index, expressed as a percentage of the original nitrogen content of the sample, is more than 40%, and assigning the thus obtained area as under-processed;
   d) determining an area in the plot obtained in b), where the ratio of the reactive amount of lysine to the total amount of lysine is less than 90%, a value of the protein dispersibility index, expressed as a percentage of the original nitrogen content of the sample, is less than 15%, and/or a value of the protein solubility in alkali, expressed as a percentage of protein in the sample that is soluble in an alkaline solution, is less than 73%, and assigning the thus obtained area as over-processed;
   e) determining an area in the plot obtained in b), where a value of the trypsin inhibitor activity, expressed as mg of trypsin per g sample, is less than 4, a value of the protein solubility in alkali, expressed as a percentage of protein in the sample that is soluble in an alkaline solution, is between 73 and 85%, a value of the protein dispersibility index, expressed as a percentage of the original nitrogen content of the sample, is between 15 and 40% and/or the value of the ratio of the reactive amount of lysine to the total amount of lysine is at least 90%, and assigning the thus obtained area as adequately processed; and/or
   subtracting the areas determined in c) and d) from the plot of b) and assigning the thus obtained area as adequately processed;
   f) generating a processing scale by standardizing the areas obtained in c) to e) to equal size, sorting them from over-processing to under-processing or vice versa and assigning a continuous scale to the standardized and sorted areas;
   g) inserting the values of the parameters obtained in a1) to a3) into a power series, and obtaining a mean of the values obtained from each power series, wherein said mean is designated as the processing condition indicator (PCI); and
   h) plotting the processing conditions indicator obtained in g) into the processing scale obtained in f) to indicate whether a feedstuff raw material and/or feedstuff is over-processed, adequately processed or under-processed.

2. The method according to claim 1, further comprising
   i) determining the standardized ileal digestibility (SID) coefficient of an amino acid in a feedstuff raw material and/or feedstuff for an animal species by
      i1) quantitative analysis of the amount of said amino acid ($AA_{intake}$) in the same sample as in a);
      i2) administering said sample to the animal species and determining the endogenous loss of said amino acid ($AA_{basal,\ excret.}$) and the ileal amino acid outflow ($AA_{ileal,\ outflow}$); and
      i3) inserting the values of the parameters obtained in i1) and i2) into formula (II):

$$SID\ [\%] = \left[\frac{AA_{intake} - (AA_{ileal,outflow} - AA_{basal,excret.})}{AA_{intake}}\right] \times 100, \quad (II)$$

and
- j) plotting the standardized ileal digestibility coefficient obtained in i) as a function of the processing conditions indicator obtained in g) and/or expressing said standard ileal digestibility coefficient in a calibration equation as a function of the processing conditions indicator obtained in g).

3. The method according to claim 2, wherein the animal species is an omnivore, a carnivore, a herbivore and/or a ruminant.

4. A computer-implemented method for assessing processing influences on nutritional value of a feedstuff raw material and/or feedstuff, the method comprising
- A) subjecting a sample of the same feedstuff raw material and/or feedstuff as in a) of the method according to claim 1 to near-infrared (NIR) spectroscopy;
- B) matching the absorption intensities at the respective wavelengths or wavenumbers in the NIR spectrum obtained in A) with the corresponding parameters and their values determined in a1) to a3); and
- C) plotting the matching of B) as a calibration graph and/or expressing the parameters determined in a1) to a3) in a calibration equation as a function of the absorption intensities at the respective wavelengths or wavenumbers matched in B).

5. The computer-implemented method according to claim 4, further comprising
- D) matching the absorption intensities at the respective wavelengths or wavenumbers in the NIR spectrum of a sample obtained in B) with the processing conditions indicator obtained for the same sample in g); and
- E) plotting the matching of D) as a calibration graph and/or expressing the processing conditions indicator in a calibration equation as a function of the absorptions intensities at the respective wavelengths or wavenumbers matched in D).

6. The computer-implemented method according to claim 5, wherein the calibration graphs and/or the calibration equations of C) and/or of E) are stored on a computer or a cloud.

7. The computer-implemented method according to claim 4, further comprising
- F) subjecting a sample of a feedstuff raw material and/or feedstuff of unknown origin or of the same origin as in a) to NIR spectroscopy;
- G) reading off the values of at least one of the parameters of a1) to a3) matching to the absorptions in the NIR spectrum obtained in F) from the calibration graph of C), and/or inserting the absorption intensities at the respective wavelengths or wavenumbers in the NIR spectrum obtained in F) into the calibration equation of C) to obtain the values for the parameters of a1) to a3);
- H) inserting the values for the parameters obtained in G) into power series and obtaining the mean of the values obtained from each power series, wherein said mean is designated as the processing condition indicator (PCI); and/or
- I) reading off the PCI from the calibration graph of E) and/or inserting the absorption intensities at the respective wavelengths or wavenumbers into the calibration equation of E) to obtain the processing conditions indicator; and
- J) plotting the processing conditions indicator obtained in H) and/or I) into the processing scale to indicate whether a feedstuff raw material and/or feedstuff is over-processed, adequately-processed or under-processed.

8. The computer-implemented method according to claim 7, wherein in G) the same parameters as in a1) to a3) are obtained.

9. The computer-implemented method according to claim 7, further comprising
- K) inserting the processing condition indicator obtained in H) into the calibration equation of j) and/or reading off the functional value for the processing conditions indicator obtained in I) to obtain a specific digestibility coefficient ($D_{AA}$) of an amino acid in the feedstuff raw material and/or feedstuff of F).

10. The computer-implemented method according to claim 9, further comprising
- L) determining a differential amount between the desired value and the real value for the amount of an amino acid in a feedstuff raw material and/or feedstuff from the difference between a maximum of an ileal digestibility coefficient of said amino acid and the specific digestibility coefficient of said amino acid obtained in K).

11. The computer-implemented method according to claim 10, further comprising
- M) determining the digestible amount of an amino acid in a sample of a feedstuff raw material and/or feedstuff by multiplying the amount of said amino acid in the sample of a feedstuff raw material and/or feedstuff obtained in G) with the specific digestibility coefficient obtained in K).

12. A process for preparing a feedstuff, the process comprising
- F) to L) of the computer-implemented method according to claim 10, and
- at least one of
- N) further processing the feedstuff raw material and/or feedstuff, if the feedstuff raw material and/or feedstuff is indicated as under-processed, and
- O) supplementing the differential amount of an amino acid obtained in L) to the feedstuff raw material and/or feedstuff, if the feedstuff raw material and/or feedstuff is indicated as over-processed.

13. The method according to claim 1, wherein the feedstuff raw material and/or feedstuff is soy, soybeans, or a soybean product.

14. The method according to claim 1,
wherein the quantitative analysis of the reactive amount of lysine in a2) comprises:
- (i) incubating the sample in O-methylisourea;
- (ii) analyzing the sample from (i) for homoarginine;
- (iii) derivatizing the sample from (ii) with ninhydrin;
- (iv) measuring absorbance of the sample from (iii) at a wavelength of 570 nm;
- (v) subjecting the sample from (iv) to a hydrolysis;
- (vi) determining a weight and a molar quantity of homoarginine in the sample from (v); and
- (vii) determining the reactive amount of lysine from the molar quantity of homoarginine obtained in (vi).

* * * * *